United States Patent
Colonna De Lega et al.

(10) Patent No.: US 7,924,435 B2
(45) Date of Patent: Apr. 12, 2011

(54) APPARATUS AND METHOD FOR MEASURING CHARACTERISTICS OF SURFACE FEATURES

(75) Inventors: Xavier Colonna De Lega, Middletown, CT (US); Peter De Groot, Middletown, CT (US)

(73) Assignee: Zygo Corporation, Middlefield, CT (US)

( * ) Notice: Subject to any disclaimer, the term of this patent is extended or adjusted under 35 U.S.C. 154(b) by 590 days.

(21) Appl. No.: 11/963,693

(22) Filed: Dec. 21, 2007

(65) Prior Publication Data

US 2008/0174784 A1   Jul. 24, 2008

Related U.S. Application Data

(60) Provisional application No. 60/876,748, filed on Dec. 22, 2006.

(51) Int. Cl.
   *G01B 11/02* (2006.01)
(52) U.S. Cl. .................................................. 356/511
(58) Field of Classification Search .................. 356/72, 356/73, 489, 495, 503, 514, 516, 511
   See application file for complete search history.

(56) References Cited

U.S. PATENT DOCUMENTS

| | | |
|---|---|---|
| 2,612,074 A | 9/1952 | Mirau |
| 4,188,122 A | 2/1980 | Massie et al. |
| 4,199,219 A | 4/1980 | Suzki et al. |
| 4,340,306 A | 7/1982 | Balasubramanian |
| 4,355,903 A | 10/1982 | Sandercock |
| 4,523,846 A | 6/1985 | Breckinridge et al. |
| 4,576,479 A | 3/1986 | Downs |
| 4,583,858 A | 4/1986 | Lebling et al. |
| 4,618,262 A | 10/1986 | Maydan et al. |
| 4,639,139 A | 1/1987 | Wyant et al. |
| 4,660,980 A | 4/1987 | Takabayashi et al. |
| 4,710,642 A | 12/1987 | McNeil |
| 4,806,018 A | 2/1989 | Falk |
| 4,818,110 A | 4/1989 | Davidson |
| 4,869,593 A | 9/1989 | Biegen |
| 4,923,301 A | 5/1990 | White |
| 4,948,253 A | 8/1990 | Biegen |

(Continued)

FOREIGN PATENT DOCUMENTS

EP   0 397 388   11/1990

(Continued)

OTHER PUBLICATIONS

Office Action for U.S. Appl. No. 11/335,871 dated Nov. 21, 2008.

(Continued)

*Primary Examiner* — Tarifur Chowdhury
*Assistant Examiner* — Jonathan M Hansen
(74) *Attorney, Agent, or Firm* — Fish & Richardson P.C.

(57) ABSTRACT

An apparatus is disclosed which includes an interferometry system configured to operate in a first mode to produce a first set of multiple interferometry signals corresponding to different illumination angles of a test object by test light and in a second mode produce a second set of multiple interferometry signals corresponding to different surface locations of a test object. An electronic processor coupled to the interferometry system is configured to receive the first set of interferometry signals and programmed to compare information derivable from the first set of multiple interferometry signals to information corresponding to multiple models of the test object to determine information related to one or features of the test object, and output the information. In some embodiments, the features include an under-resolved feature.

65 Claims, 17 Drawing Sheets

U.S. PATENT DOCUMENTS

| | | | |
|---|---|---|---|
| 4,964,726 A | 10/1990 | Kleinknecht et al. | |
| 4,999,014 A | 3/1991 | Gold et al. | |
| 5,042,949 A | 8/1991 | Greenberg et al. | |
| 5,042,951 A | 8/1991 | Gold et al. | |
| 5,073,018 A | 12/1991 | Kind et al. | |
| 5,112,129 A | 5/1992 | Davidson et al. | |
| 5,129,724 A | 7/1992 | Brophy et al. | |
| 5,133,601 A | 7/1992 | Cohen et al. | |
| 5,135,307 A | 8/1992 | De Groot et al. | |
| 5,153,669 A | 10/1992 | DeGroot | |
| 5,164,790 A | 11/1992 | McNeil et al. | |
| 5,166,751 A | 11/1992 | Massig | |
| 5,173,746 A | 12/1992 | Brophy | |
| 5,194,918 A | 3/1993 | Kino et al. | |
| 5,241,369 A | 8/1993 | McNeil et al. | |
| 5,301,010 A | 4/1994 | Jones et al. | |
| 5,355,221 A | 10/1994 | Cohen et al. | |
| 5,384,717 A | 1/1995 | Ebenstein | |
| 5,386,119 A | 1/1995 | Ledger | |
| 5,390,023 A | 2/1995 | Biegen | |
| 5,398,113 A | 3/1995 | De Groot | |
| 5,402,234 A | 3/1995 | Deck | |
| 5,459,564 A | 10/1995 | Chivers | |
| 5,471,303 A | 11/1995 | Ai et al. | |
| 5,481,811 A | 1/1996 | Smith | |
| 5,483,064 A | 1/1996 | Frey et al. | |
| 5,539,517 A | 7/1996 | Cabib et al. | |
| 5,543,841 A | 8/1996 | Kanamori | |
| 5,555,471 A | 9/1996 | Xu et al. | |
| 5,587,792 A | 12/1996 | Nishizawa et al. | |
| 5,589,938 A | 12/1996 | Deck | |
| 5,596,406 A * | 1/1997 | Rosencwaig et al. | 356/327 |
| 5,602,643 A | 2/1997 | Barrett | |
| 5,633,714 A | 5/1997 | Nyyssonen | |
| 5,640,270 A | 6/1997 | Aziz et al. | |
| 5,703,692 A | 12/1997 | McNeil et al. | |
| 5,757,502 A | 5/1998 | Weling | |
| 5,774,224 A | 6/1998 | Kerstens | |
| 5,777,740 A | 7/1998 | Lacey et al. | |
| 5,777,742 A | 7/1998 | Marron | |
| 5,784,164 A | 7/1998 | Deck et al. | |
| 5,856,871 A | 1/1999 | Cabib et al. | |
| 5,867,276 A | 2/1999 | McNeil et al. | |
| 5,880,838 A | 3/1999 | Marx et al. | |
| 5,900,633 A | 5/1999 | Solomon et al. | |
| 5,912,741 A | 6/1999 | Carter et al. | |
| 5,923,423 A | 7/1999 | Sawatari et al. | |
| 5,943,134 A | 8/1999 | Yamaguchi et al. | |
| 5,953,124 A | 9/1999 | Deck | |
| 5,956,141 A | 9/1999 | Hayashi | |
| 5,959,735 A | 9/1999 | Maris et al. | |
| 5,963,329 A | 10/1999 | Conrad et al. | |
| 6,028,670 A | 2/2000 | Deck | |
| 6,160,621 A | 12/2000 | Perry et al. | |
| 6,172,452 B1 | 1/2001 | Itaya et al. | |
| 6,242,739 B1 | 6/2001 | Cherkassky | |
| 6,249,351 B1 | 6/2001 | De Groot | |
| 6,259,521 B1 | 7/2001 | Miller et al. | |
| 6,275,297 B1 | 8/2001 | Zalicki | |
| 6,377,349 B1 | 4/2002 | Fercher | |
| 6,381,009 B1 | 4/2002 | McGahan | |
| 6,392,749 B1 | 5/2002 | Meeks et al. | |
| 6,417,109 B1 | 7/2002 | Jordan et al. | |
| 6,429,943 B1 | 8/2002 | Opsal et al. | |
| 6,449,048 B1 | 9/2002 | Olszak | |
| 6,449,066 B1 | 9/2002 | Arns et al. | |
| 6,483,580 B1 | 11/2002 | Xu et al. | |
| 6,500,591 B1 | 12/2002 | Adams | |
| 6,507,405 B1 | 1/2003 | Grek et al. | |
| 6,525,825 B2 | 2/2003 | de Groot | |
| 6,545,761 B1 | 4/2003 | Aziz et al. | |
| 6,545,763 B1 | 4/2003 | Kim et al. | |
| 6,590,656 B2 | 7/2003 | Xu et al. | |
| 6,597,460 B2 | 7/2003 | Groot et al. | |
| 6,611,330 B2 | 8/2003 | Lee et al. | |
| 6,624,894 B2 | 9/2003 | Olszak et al. | |
| 6,633,389 B1 | 10/2003 | Poris et al. | |
| 6,633,831 B2 | 10/2003 | Nikoonahad et al. | |
| 6,636,322 B1 | 10/2003 | Terashita | |
| 6,694,284 B1 | 2/2004 | Nikoonahad et al. | |
| 6,714,307 B2 | 3/2004 | De Groot et al. | |
| 6,721,094 B1 | 4/2004 | Sinclair et al. | |
| 6,741,357 B2 | 5/2004 | Wang et al. | |
| 6,741,360 B2 | 5/2004 | D'Agraives et al. | |
| 6,775,006 B2 | 8/2004 | De Groot et al. | |
| 6,775,009 B2 | 8/2004 | Hill | |
| 6,798,511 B1 | 9/2004 | Zhan et al. | |
| 6,822,745 B2 | 11/2004 | De Groot et al. | |
| 6,856,384 B1 * | 2/2005 | Rovira | 356/73 |
| 6,888,638 B1 | 5/2005 | Hill | |
| 6,891,627 B1 | 5/2005 | Levy et al. | |
| 6,909,509 B2 | 6/2005 | DeGroot | |
| 6,925,860 B1 | 8/2005 | Poris et al. | |
| 6,940,604 B2 | 9/2005 | Jung et al. | |
| 6,956,658 B2 | 10/2005 | Meeks et al. | |
| 6,956,660 B2 | 10/2005 | Meeks et al. | |
| 6,985,232 B2 | 1/2006 | Sezginer | |
| 6,989,905 B2 | 1/2006 | De Groot | |
| 6,999,180 B1 | 2/2006 | Janik et al. | |
| 7,012,700 B2 | 3/2006 | de Groot et al. | |
| 7,018,271 B2 | 3/2006 | Wiswesser et al. | |
| 7,038,850 B2 | 5/2006 | Chang et al. | |
| 7,046,371 B2 | 5/2006 | De Lega et al. | |
| 7,061,623 B2 | 6/2006 | Davidson | |
| 7,068,376 B2 | 6/2006 | De Groot | |
| 7,088,451 B2 | 8/2006 | Sezginer | |
| 7,102,761 B2 | 9/2006 | De Lega et al. | |
| 7,106,454 B2 | 9/2006 | De Groot et al. | |
| 7,119,909 B2 | 10/2006 | Unruh et al. | |
| 7,139,081 B2 | 11/2006 | De Groot | |
| 7,139,083 B2 | 11/2006 | Fielden et al. | |
| 7,142,311 B2 | 11/2006 | De Lega | |
| 7,177,030 B2 | 2/2007 | Leizerson | |
| 7,205,518 B2 | 4/2007 | Neuvonen | |
| 7,239,398 B2 | 7/2007 | De Groot et al. | |
| 7,271,918 B2 | 9/2007 | De Groot et al. | |
| 7,283,248 B2 | 10/2007 | Hill | |
| 7,289,225 B2 | 10/2007 | De Groot | |
| 7,298,494 B2 | 11/2007 | De Groot | |
| 7,304,747 B2 | 12/2007 | De Lega | |
| 7,315,382 B2 | 1/2008 | De Groot | |
| 7,324,210 B2 | 1/2008 | De Groot et al. | |
| 7,324,214 B2 | 1/2008 | De Groot et al. | |
| 7,428,057 B2 | 9/2008 | De Lega et al. | |
| 7,566,517 B1 * | 7/2009 | Adel et al. | 430/5 |
| 2002/0015146 A1 | 2/2002 | Meeks et al. | |
| 2002/0135775 A1 | 9/2002 | De Groot et al. | |
| 2002/0148955 A1 | 10/2002 | Hill | |
| 2002/0196450 A1 | 12/2002 | Olszak et al. | |
| 2003/0011784 A1 | 1/2003 | de Groot et al. | |
| 2003/0048458 A1 | 3/2003 | Mieher et al. | |
| 2003/0075721 A1 | 4/2003 | Li | |
| 2003/0112444 A1 | 6/2003 | Yang et al. | |
| 2003/0137671 A1 | 7/2003 | De Groot et al. | |
| 2003/0197871 A1 | 10/2003 | De Groot | |
| 2004/0027576 A1 | 2/2004 | De Groot et al. | |
| 2004/0075843 A1 | 4/2004 | Marron et al. | |
| 2004/0085544 A1 * | 5/2004 | De Groot | 356/497 |
| 2004/0185582 A1 | 9/2004 | Kueny | |
| 2004/0189999 A1 | 9/2004 | de Groot et al. | |
| 2004/0233442 A1 | 11/2004 | Mieher et al. | |
| 2004/0233444 A1 | 11/2004 | Mieher et al. | |
| 2004/0246493 A1 | 12/2004 | Kim et al. | |
| 2005/0024773 A1 | 2/2005 | Lille | |
| 2005/0057757 A1 | 3/2005 | Colonna de Lega et al. | |
| 2005/0068540 A1 | 3/2005 | De Groot et al. | |
| 2005/0073692 A1 | 4/2005 | De Groot et al. | |
| 2005/0078318 A1 | 4/2005 | De Groot | |
| 2005/0078319 A1 | 4/2005 | De Groot | |
| 2005/0088663 A1 | 4/2005 | De Groot et al. | |
| 2005/0146727 A1 | 7/2005 | Hill | |
| 2005/0179911 A1 | 8/2005 | Boomgarden et al. | |
| 2005/0225769 A1 | 10/2005 | Bankhead et al. | |
| 2005/0237534 A1 | 10/2005 | Deck | |
| 2005/0237537 A1 | 10/2005 | Leizerson et al. | |
| 2006/0012582 A1 | 1/2006 | De Lega | |
| 2006/0045327 A1 * | 3/2006 | Dang et al. | 382/151 |

| | | | |
|---|---|---|---|
| 2006/0072104 | A1 | 4/2006 | Engel et al. |
| 2006/0119841 | A1 | 6/2006 | Saunders et al. |
| 2006/0126079 | A1* | 6/2006 | Bareket et al. ............... 356/625 |
| 2006/0158657 | A1 | 7/2006 | De Lega et al. |
| 2006/0158658 | A1 | 7/2006 | De Lega et al. |
| 2006/0158659 | A1* | 7/2006 | Colonna De Lega et al. ............... 356/497 |
| 2006/0170932 | A1 | 8/2006 | Hayashi et al. |
| 2006/0187465 | A1 | 8/2006 | De Groot |
| 2006/0262321 | A1 | 11/2006 | De Groot |
| 2007/0008551 | A1 | 1/2007 | Tang |
| 2007/0046953 | A1 | 3/2007 | de Groot et al. |
| 2007/0081167 | A1 | 4/2007 | De Groot |
| 2007/0086013 | A1 | 4/2007 | De Lega et al. |
| 2007/0091317 | A1 | 4/2007 | Freischlad et al. |
| 2007/0091318 | A1 | 4/2007 | Freishlad et al. |
| 2007/0091940 | A1 | 4/2007 | Jameson |
| 2007/0097380 | A1 | 5/2007 | De Groot et al. |
| 2007/0127036 | A1 | 6/2007 | Liao et al. |
| 2007/0139656 | A1 | 6/2007 | Wan |
| 2007/0247637 | A1 | 10/2007 | De Groot |
| 2008/0018901 | A1 | 1/2008 | de Groot |
| 2008/0088849 | A1 | 4/2008 | de Lega et al. |
| 2008/0174784 | A1 | 7/2008 | de Lega et al. |

FOREIGN PATENT DOCUMENTS

| | | |
|---|---|---|
| EP | 0 549 166 | 6/1993 |
| EP | 0 617 255 | 9/1994 |
| EP | 0 929 094 | 7/1999 |
| GB | 4108944 | 9/1992 |
| GB | 4309056 | 9/1994 |
| GB | 2385417 | 8/2003 |
| JP | 8327327 | 12/1996 |
| JP | 09-218016 | 8/1997 |
| JP | 2000121317 | 4/2000 |
| JP | 2000-180124 | 6/2000 |
| JP | 2001-272603 | 10/2001 |
| JP | 2001-141652 | 5/2009 |
| KR | 20000061037 | 10/2000 |
| WO | WO 93/24805 | 12/1993 |
| WO | WO 94/00733 | 1/1994 |
| WO | WO 02/082008 | 10/2002 |
| WO | WO 03/036229 | 5/2003 |
| WO | WO 03/062802 | 7/2003 |
| WO | WO 2004/023071 | 3/2004 |
| WO | WO 2005/029192 | 3/2005 |

OTHER PUBLICATIONS

PCT Search Report dated Jun. 10, 2008 by ISA/RO.
Supplementary European Search Report dated Aug. 12, 2010, corresponding to European Patent Appln. No. 07871735.2.
US 7,151,607, 12/2008, De Groot et al. (withdrawn).
Abdulhalim; "Spectroscopic interference microscopy technique for measurement of layer parameters", Meas. Sci. Technol., vol. 12, pp. 1996-2001 (2001).
Akcay et al., "Spectral shaping to improve the point spread function in optical coherence tomography", Optics Letters, vol. 28, No. 20, pp. 1921-1923 (Oct. 15, 2003).
Azzam et al,."Ellipsometric function of a film-substrate system: Applications to the design of reflection-type optical devices and to ellipsometry", Journal of the Optical Society of America, vol. 5, No. 3, pp. 252-260 (1975).
Azzam et al., "Reflection and Transmission of Polarized Light by Stratified Planar Structures", Ellipsometry and Polarized Light, Elsevier Science B.V. ISBN 0 444 87016 4 (Paperback) pp. 267-363 (1987).
Bashkansky et al., "Signal Processing for Improving Field Cross-correlation Function in Optical Coherence Tomography", Supplement to Optics & Photonics News, 9(5) (May 1998).
Biegen, "Determination of the Phase Change on Reflection from Two-beam Interference," Optics Letters, 19:21:1690-1692, Nov. 1, 1994.
Bishop, et al., "Grating line shape characterization using scatterometry," SPIE 1545, 64-73 (1991).
Bosseboeuf et al., Application of microscopic interferometry techniques in the MEMS field, Proc. SPIE, 5145, pp. 1-16 (2003). cited by other.

Chim, S. S. C. and Kino, G. S., "Three-Dimensional Image Realization in Interference Microscopy", Applied Optics, May 10, 1992, vol. 31, No. 14.
Creath, "Step height measurement using two-wavelength phase-shifting interferometry", Applied Optics, vol. 26, No. 14, pp. 2810-2816 (Jul. 15, 1987).
Danielson et al., "Absolute Optical Ranging Using Low Coherence Interferometry," Applied Optics, 30:21:2975-2979, Jul. 20, 1991.
Davidson et al., "An Application of Interference Microscopy to Integrated Circuit Inspection and Metrology", Proceedings of SPIE, vol. 775, pp. 233-247 (1987).
de Groot et al., "Angle-resolved three-dimensional analysis of surface films by coherence scanning interferometry", Optics Letters, vol. 32, No. 12, pp. 1638-1640 (Jun. 15, 2007).
de Groot et al., "Determination of fringe order in white-light interference microscopy", Appl. Opt., 41(22) pp. 4571-4578 (2002).
de Groot et al., "Signal modeling for low coherence height-scanning interference microscopy", Applied Optics, vol. 43 No. 25, pp. 4821-4830 (Sep. 1, 2004).
de Groot et al., "Signal modeling for modern interference microscopes", SPIE Proceedings vol. 5457, pp. 26-34 (2004).
de Groot et al.; "Three-dimensional imaging by sub-Nyquist sampling of white-light interfergrams"; Optics Letters vol. 18, No. 17; pp. 1462-1464, Sep. 1, 1993.
de Groot, "Extending the unambiguous range of two-color interferometers", Applied Optics, vol. 33, No. 25, pp. 5948-5953 (Sep. 1, 1994).
de Groot, "Derivation of algorithms for phase-shifting interferometry using the concept of a data-sampling window", Appl. Opt., 34(22), p. 4723-4730 (1995).
de Groot, "Three-color laser-diode interferometer", Applied Optics, vol. 30, No. 25, pp. 3612-3616 (Sep. 1, 1991).
de Groot, P., "Phase-shift calibration errors in interometers with spherical Fizeua cavities," Applied Optics, vol. 34:16, pp. 2856-2863 (Jun. 1, 1995).
de Lega, X., et al., "Optical topography measurement of patterned wafers," American Institute of Physics Conference Proceedings, vol. 788, pp. 432-436 (2005).
Debnath, S.K., et al., "Spectrally resolved phase-shifting interferometry of transparent thin films: sensitivity of thickness measurements," Appl. Opt. 45, 34 8636-8640 (2006).
Deck et al., "Two-color light-emitting-diode source for high-precision phase-shifting interferometry", Optics Letters, vol. 18, No. 22, pp. 1899-1901 (Nov. 15, 1993).
Dresel et al., "Three Dimensional Sensing of Rough Surfaces by Coherence Radar, " Applied Optics, 31:7:919-925, Mar. 1, 1992.
Encyclopedia of Laser Physics and Technology, http:\\www.rp-photonics.com\coherence.html, Mar. 14, 2008.
Encyclopedia of Laser Physics and Technology, http:\\www.rp-photonics.com\single mode fibers.html, Mar. 14, 2008.
Encyclopedia of Laser Physics and Technology, http:\\www.rp-photonics.com\photonic crystal fibers.html, Mar. 14, 2008.
Encyclopedia of Laser Physics and Technology, http:\\www.rp-photonics.com\supercontinuum generation.html, Mar. 14, 2008.
Feke, Gilbert D. et al., "Interferometric back focal plane microellipsometry", Applied Optics, vol. 37, No. 10, pp. 1796-1802 (Apr. 1, 1998).
Flournoy et al., "White-light interferometric thickness gauge", Appl. Opt., 11(9), pp. 1907-1915 (1972).
Gale et al., "Linnik microscope imaging of integrated circuit structures", Applied Optics vol. 35, No. 1, pp. 131-148 (Jan. 1, 1996).
Ghiglia et al., "Quality-Guided Path Following", Two-Dimensional Phase Unwrapping—Theory, Algorithms and Software, John Wiley & Sons publishers, ISBN 0-471-24935-1, pp. 122-136 (1998).
Greivenkamp, "Generalized data reduction for heterodyne interferometry", Opt. Eng., vol. 23 No. 4, pp. 350-352 (Jul./Aug. 1984).
Hausler et al., "Coherence Radar and Spectral Radar—New Tools for Dermatological Diagnosis", Journal of Biomedical Optics, vol. 3, No. 1, pp. 21-31 (Jan. 1998).
Hecht, "Basics of Coherence Theory," Optics, 2nd Ed., Addison Wesley, pp. 516-517 (1987).

Holmes et al., "Scanning microellipsometry for extraction of true topography", Electronics Letters, vol. 31, No. 5, pp. 358-359 (Mar. 2, 1995).

Kim, Seung-Woo et al., "Thickness-profile measurement of transparent thin-film layers by white-light scanning interferometry", Applied Optics, vol. 38, No. 28, pp. 5968-5973 (Oct. 1, 1999).

Kino et al., "Mirau Correlation Microscope," Applied Optics, 29:26:3775-3783, Sep. 10, 1990.

Kleinknecht, et al., "Linewidth measurement on IC masks and wafers by grating test patterns," Appl. Opt. 19(4), 523-533 (1980).

Kohlhaas, A. Fromchen, C. and Brinkmeyer, E., "High-Resolution OCDR for Testing Integrated-Optical Waveguides: Dispersion-Corrupted Experimental Data Corrected by a Numerical Algorithm", Journal of Lightwave Technology, Nov. 1991, vol. 9, No. 11.

Kujawinska, Malgorzata, "Spatial Phase Measurement Methods", Interferogram Analysis: Digital Fringe Pattern Measurement Techniques, IOP Publishing Ltd. 1993, pp. 141-193.

Larkin, "Efficient nonlinear algorithm for envelope detection in white light interferometry", J. Opt. Soc. Am A4, pp. 832-843 (1996).

Lee et al., "Profilometry with a coherence scanning microscope", Appl. Opt., 29(26), pp. 3784-3788 (1990).

Lee-Bennett, "Advances in non-contacting surface metrology", OF&T Workshop, paper OTuC1 (2004).

Leonhardt et al., "Micro-Ellipso-Height-Profilometry", Optics Communications, vol. 80, No. 3, 4, pp. 205-209 (Jan. 1, 1991).

Liu et al., "Common path interferometric microellipsometry", SPIE, vol. 2782, pp. 635-645 (1996).

Lyakin et al., "The interferometric system with resolution better than coherence length for determination of geometrical thickness and refractive index of a layer object", Proceedings of the SPIE—The International Society for Optical Engineering SPIE-IN, 2003.

Morgan, "Least-Squares estimation in phase-measurement interferometry", Apt. Let., 7(8), pp. 368-370 (1982).

Naqvi, et al., "Linewidth measurement of gratings on photomasks: a simple technique," Appl. Opt., 31(10), 1377-1384 (1992).

Ngoi et al., "Phase-shifting interferometry immune to vibration", Applied Optics, vol. 40, No. 19, pp. 3211-3214 (2001).

Novak et al., "Template-based software for accurate MEMS characterization", Proceedings of SPIE, Fol. 4980, pp. 75-80 (2003).

Onodera et al., "Two-wavelength interferometry that uses a Fourier-transform method", Applied Optics, vol. 37, No. 34, pp. 7988-7994 (Dec. 1, 1998).

Oppenheim et al., "10.3: The time-dependent Fourier Transform", Discrete-Time Signal Processing, 2.sup.nd Edition, pp. 714-722 (Prentice Hall, New Jersey, 1999). cited by other.

Park et al., "Direct quadratic polynomial fitting for fringe peak detection of white light scanning interferograms", Opt. Eng, 39(4), pp. 952-959 (2000).

Pelligrand, S. et al., "Mesures 3D de topographies et de vibrations a l'echelle (sub)micrometrique par microscopie optique interferometrique", Proc. Club CMOI, Methodes et Techniques Optiques pour l'Industrie (2002).

Peng, S.T., et al., "Theory of Periodic Dielect Waveguides," IEEE Trans Microwave Theory and Technique MTT-23(1), 123-133 (1975).

Pfortner et al., "Red-green-blue interferometer for the metrology of discontinuous structures", Applied Optics, vol. 42, No. 4, pp. 667-673 (Feb. 1, 2003).

Pluta, Maksymilian, "Advanced Light Microscopy", vol. 3, (Elsevier, Amsterdam, 1993) pp. 265-271.

Press et al., "Linear Correlation", Numerical Recipes in C, Cambridge University Press, 2.sup.ncl Edition, pp. 636-639 (1992).

Raymond, C.J., "Scatterometry for Semiconductor Metrology," in Handbook of silicon semiconductor metrology, A.J. Deibold, Ed. (Marcel Dekker, Inc., New York 2001).

Raymond, et al., "Scatterometry for CD measurements of etched structures," SPIE 2725, 720-728 (1996).

Rosencwaig, Allan et al., "Beam profile reflectometry: A new technique for dielectric film measurements", Applied Physics Letters, vol. 60, No. 11, pp. 1301-1303 (Mar. 16, 1992).

Sandoz et al., "High-resolution profilometry by using phase calculation algorithms for spectroscopic analysis of white-light interferograms", Journal of Modern Optics, vol. 43, No. 4 , pp. 701-708 (1996).

Sandoz et al., "Optical implementation of frequency domain analysis for white light interferometry", Proceedings SPIE, vol. 2545, pp. 221-228 (Jun. 1995).

Sandoz et al., "Processing of white light correlograms: simultaneous pahse and envelope measurements by wavelet transformation", SPIE, 3098, pp. 73-82 (1997).

Sandoz, Patrick "Wavelet transform as a processing tool in white-light interferometry", Optics Letters, vol. 22, No. 14, pp. 1065-1067 (Jul. 15, 1997).

Schmit, J. et al., "Extended averaging technique for derivation of error-compensating algorithms in phase-shifting interferometry," Applied Optics, vol. 34:19, pp. 3610-3619 (Jul. 1, 1995).

Schnell et al., "Dispersive white-light interferometry for absolute distance measurement with dielectric multilayer systems on the target", Optics Letters, vol. 21, No. 7, pp. 528-530 (Apr. 1996).

Schwider et al., "Dispersive interferometric profilometer", Optics Letters, vol. 19, No. 13, pp. 995-997 (Jul. 1994).

See et al., "Scanning optical microellipsometer for pure surface profiling", Applied Optics, vol. 35, No. 34, pp. 6663-6668 (Dec. 1, 1996). cited by other.

Shatalin, S. V. et al., "Reflection conoscopy and micro-ellipsometry of isotropic thin film structures", Journal of Microscopy, vol. 179, Part 3, pp. 241-252 (Sep. 1995).

Sheppard et al., "Effect of numerical aperture on interference fringe spacing", Applied Optics, vol. 34, No. 22, pp. 4731-4734 (Aug. 1, 1995).

Totzeck, "Numerical simulation of high-NA quantitative polarization microscopy and corresponding near-fields", Optik, vol. 112, No. 9, pp. 399-406 (2001).

Tripathi et al., "Spectral shaping for non-Gaussian source spectra in optical coherence tomography", Optics Letters, vol. 27, No. 6, pp. 406-408 (2002).

Tzannes et al., Measurement of the modulation transfer function of infrared cameras, Optical Engineering, vol. 34, No. 6, pp. 1808-1817 (Jun. 1995). cited by other.

Willenborg et al, "A novel micro-spot dielectric film thickness measurement system", SPIE, vol. 1594, pp. 322-333 (1991).

Wyant, "Phase shifting interferometry" (1998).

Youngquist, R. C. Carr, S. and Davies, D. E. N., "Optical Coherence-Domain Reflectometry: a New Optical Evaluation Technique", Optical Letters, Mar. 1987, vol. 12, No. 3.

Zhan, Q., et al., "Measurement of surface features beyond the diffraction limit with an imaging ellipsometer," Opt. Lett. 27, 821-823 (2002).

International Search Report, Jun. 10, 2008.

* cited by examiner

Complex reflectance signals – measured and library (best match)

445 nm 50°

516 nm 50°

569 nm 50°

Dielectric
Thickness (t) ~ 100 – 700nm

Trench Depth (d) ~ 100 – 400nm

Trench Width (w) ~ 100 – 500nm

Density (Width/Pitch) ~ 30 – 90%

Note:
The Oxide Trenches may be over solid Cu pads capped with SiON.

1401

Poly Si Thickness ~ 30 – 150 nm
Top CD ($T_{cd}$) ~ 30 – 100nm
Bottom CD ($B_{cd}$) ~ 30 – 100nm
Note: $B_{cd} =< T_{cd}$ Nickel Silicide
Nickel Gate Electrode
1.2 nm SiO₂ Gate Oxide
Strained Silicon

APPARATUS AND METHOD FOR MEASURING CHARACTERISTICS OF SURFACE FEATURES

CROSS-REFERENCE TO RELATED APPLICATIONS

This application claims priority to Provisional Patent Application No. 60/876,748, entitled "APPARATUS AND METHOD FOR MEASURING CHARACTERISTICS OF SURFACE FEATURES," filed on Dec. 22, 2006, the entire contents of which is incorporated herein by reference.

BACKGROUND

The disclosure relates to using scanning interferometry to measure surface characteristics of objects having complex surface structures, such as thin film(s), discrete structures of dissimilar materials, or discrete structures that are under-resolved by the optical resolution of an interference microscope. Such measurements are relevant to the characterization of flat panel display components, semiconductor wafer metrology, and in-situ thin film and dissimilar materials analysis.

Interferometric techniques are commonly used to measure the profile of a surface of an object. To do so, an interferometer combines a measurement wavefront reflected from the surface of interest with a reference wavefront reflected from a reference surface to produce an interferogram. Fringes in the interferogram are indicative of spatial variations between the surface of interest and the reference surface.

Typically, a scanning interferometer scans the optical path length difference (OPD) between the reference and measurement legs of the interferometer over a range comparable to, or larger than, the coherence length of the interfering wavefronts, to produce a scanning interferometry signal for each camera pixel used to measure the interferogram. A limited coherence length can be produced, for example, by using a white-light source, which is referred to as scanning white light interferometry (SWLI). A typical scanning white light interferometry signal is a few fringes localized near the zero optical path difference (OPD) position. The signal is typically characterized by a sinusoidal carrier modulation (the "fringes") with bell-shaped fringe-contrast envelope. The conventional idea underlying SWLI metrology is to make use of the localization of the fringes to measure surface profiles.

SWLI processing techniques include two principle trends. The first approach is to locate the peak or center of the envelope, assuming that this position corresponds to the zero optical path difference (OPD) of a two-beam interferometer for which one beam reflects from the object surface. The second approach is to transform the signal into the frequency domain and calculate the rate of change of phase with wavelength, assuming that an essentially linear slope is directly proportional to object position. See, for example, U.S. Pat. No. 5,398,113 to Peter de Groot. This latter approach is referred to as Frequency Domain Analysis (FDA).

Scanning interferometry can be used to measure surface topography and/or other characteristics of objects having complex surface structures, such as thin film(s), discrete structures of dissimilar materials, or discrete structures that are under-resolved by the optical resolution of an interference microscope. Such measurements are relevant to the characterization of flat panel display components, semiconductor wafer metrology, and in-situ thin film and dissimilar materials analysis. See, e.g., U.S. Patent Publication No. US-2004-0189999-A1 by Peter de Groot et. al. entitled "Profiling Complex Surface Structures Using Scanning Interferometry" and published on Sep. 30, 2004, the contents of which are incorporated herein by reference, and U.S. Patent Publication No. US-2004-0085544-A1 by Peter de Groot entitled "Interferometry Method for Ellipsometry, Reflectometry, and Scatterometry Measurements, Including Characterization of Thin Film Structures" and published on May 6, 2004, the contents of which are incorporated herein by reference.

Other techniques for optically determining information about an object include ellipsometry and reflectometry. Ellipsometry determines complex reflectivity of a surface when illuminated at an oblique angle, e.g. 60°, sometimes with a variable angle or with multiple wavelengths. To achieve greater resolution than is readily achievable in a conventional ellipsometer, microellipsometers measure phase and/or intensity distributions in the back focal plane of the objective, also known as the pupil plane, where the various illumination angles are mapped into field positions. Such devices are modernizations of traditional polarization microscopes or "conoscopes," linked historically to crystallography and mineralogy, which employ crossed polarizers and a Bertrand lens to analyze the pupil plane birefringent materials.

Conventional techniques used for thin film characterization (e.g., ellipsometry and reflectometry) rely on the fact that the complex reflectivity of an unknown optical interface depends both on its intrinsic characteristics (material properties and thickness of individual layers) and on three properties of the light that is used for measuring the reflectivity: wavelength, angle of incidence, and polarization state. In practice, characterization instruments record reflectivity fluctuations resulting from varying these parameters over known ranges. Optimization procedures such as least-squares fits are then used to get estimates for the unknown parameters by minimizing the difference between measured reflectivity data and a reflectivity function derived from a model of the optical structure.

Complex surface structures, e.g. patterned semiconductor wafers, may be comprised of features of dissimilar materials of various sizes from mm down to a few tens of nm in size.

SUMMARY

The inventors have realized that there is a wealth of information in a scanning interferometry signal, much of which is ignored in conventional processing. Interference signals measured in an interferometer illuminated with a spectrally broadband source can be analyzed to determine optical characteristics (i.e. under-resolved features) of an object surface that may not be fully resolved in a conventional imaging microscope. For example, information can be obtained related to dimensional parameters such as depth, width, sidewall angle, edge rounding and film structure of objects that may be smaller than one-half the wavelength of the illuminating light.

In the processing techniques described herein, information derivable from a scanning interferometry signal corresponding to the complex reflectivity of a test object for light incident at a given angle, wavelength and polarization state is compared to information corresponding to multiple models of the test object. For example, the test object can be modeled as having a range of structural features including, for example, under-resolved gratings with a range of possible depths and pitches. This comparison is repeated over a range of angles, wavelengths and polarization states to determine which of the models provides the best fit of the experimental data to theoretical predictions based on the model. The structural features of the best fit model correspond to the best estimate for the structural features of the test object.

The structural feature information determined in this manner can be used to improve the performance (e.g., accuracy, speed, etc.) of a surface profile measurement. Furthermore, surface profile information can be used to improve the performance of a surface feature measurement of the type described above. In one aspect, an interferometry system is disclosed which can perform both types of measurements, and use each measurement type to improve the other.

The measurement techniques and subsequent analysis approach described herein is applicable to several semiconductor processing steps. With the use of optical proximity corrections and/or phase shift masks, dimensions of patterned objects can be smaller than the wavelength used by the optical lithography tool. For example, 193 nm lithography tools pattern 65 nm objects in today's high volume manufacturing facilities routinely; the use of etch bias steps and hard mask structures can extend the lower limit to 45 nm and below. With the ability to print sub wavelength structural features comes the need to monitor these features and the associated etch and deposition steps. The embodiments of the current disclosure enable measurements of the under-resolved structural features.

One example of such in-process metrology measurements of semiconductor chips include using scanning interferometry measurements for non-contact surface topography measurements of semiconductor wafers during chemical mechanical polishing (CMP) of a dielectric layer on the wafer. CMP is used to create a smooth surface for the dielectric layer, suitable for precision optical lithography. Based on the results of the interferometric methods, the process conditions for CMP (e.g., pad pressure, polishing slurry composition, etc.) can be adjusted to keep surface non-uniformities within acceptable limits.

In addition to complex reflectivity, the information derivable from a scanning interferometer such as those disclosed herein can include information relating the complex reflectivity at different angles of incidence and/or at different wavelengths. For example, interferometric data can include a global phase relationship, relating the complex reflectivity at different angles of incidence and/or at different wavelengths.

In some embodiments, the comparison of experimental data to modeled data makes use of the global phase relationship. For example, the global phase relationship can provide an additional constraint to which modeled data should conform in order to be considered an accurate model of a test structure, providing more robust solutions when matching experimental data to modeled data. For example, in conventional ellipsometry, measured values of $\psi$ and $\Delta$ can be compared to modeled values of $\psi$ and $\Delta$ for a range of incident angles and/or wavelengths. It is possible that different modeled structures will result in matching values of $\psi$ and $\Delta$ over the sampled ranges, providing degenerate solutions when trying to determine the structure of the sample. Having an additional constraint, such as the global phase relationship, can lift this degeneracy because the different models that provide matching values of $\psi$ and $\Delta$ across the sampled ranges, for example, will not necessary satisfy the global phase relationship.

We now summarize various aspects and features.

In one aspect, an apparatus is disclosed which includes an interferometry system configured to operate in a first mode to produce a first set of multiple interferometry signals corresponding to different illumination angles of a test object by test light and in a second mode produce a second set of multiple interferometry signals corresponding to different surface locations of a test object. An electronic processor coupled to the interferometry system is configured to receive the first set of interferometry signals and programmed to compare information derivable from the first set of multiple interferometry signals to information corresponding to multiple models of the test object to determine information related to one or features of the test object, and output the information. In some embodiments, the features include an under-resolved feature In some embodiments, the apparatus is configured to selectively switch between the first and second modes. In some embodiments, the apparatus is configured to simultaneously provide measurements in both modes.

In some embodiments the interferometry system includes at least one electronic detector, and in the first mode different elements of the detector correspond to different illumination angles of the test surface by test light in the interferometry system. In some embodiments, the first mode corresponds to an ellipsometry mode that measures the reflectivity of the test surface over the range of angles and wavelengths for one or more selected polarizations. In some embodiments, the reflectivity is a complex reflectivity.

In some embodiments, the first mode corresponds to a reflectometry mode that measures the reflectivity of the test surface over the range of angles and wavelengths for unpolarized light. In some embodiments, the reflectivity is a complex reflectivity.

In some embodiments, the interferometry system images a pupil plane for test light directed to the test surface to the detector.

In some embodiments, the interferometry system includes at least one electronic detector, and in the second mode different elements of the detector correspond to different locations of the test surface illuminated by test light in the interferometry system. For example, In some embodiments, interferometer is configured to image the test surface to the detector. In some embodiments, the second mode is a profiling mode.

In some embodiments, the electronic processor is further configured to receive the first and second sets of interferometry signals and programmed to determine information about the test object, and output the information about the test object.

In some embodiments, the electronic processor is further configured to use the information derived in one mode of operation to assist in determining further information about the test object when using the other mode of operation. For example, in some embodiments, the electronic processor is configured to use the information related to under-resolved features of the test object determined in the first mode of operation to assist in determining further information about the test object when using the other mode of operation. For example, in some embodiments the further information includes surface topography, thin film structure, and/or etch depth. In some embodiments, the electronic processor is configured to use the information related to the surface profile of the test object determined in one mode of operation to assist in determining further information about the test object when using the other mode of operation. For example, in some embodiments, the further information includes information related to under-resolved surface features.

In some embodiments, the electronic processor is configured to derive multiple models of the test object based on the information related to under-resolved features of the test object determined in the first mode of operation and compare information derivable from the second set of multiple interferometry signals to information corresponding to the multiple models of the test object based on the information related to under-resolved features to determine further information related to the test object, and output the information. In some embodiments, the further information is information related to a surface profile.

In some embodiments, the interferometry system is further configured to selectively operate in a non-interferometric microscopy mode to measure non-interferometric optical images of the test surface.

In some embodiments, the electronic processor is configured to use the information related to under-resolved features of the test object determined in the first mode of operation to assist in determining further information about the test object when using the other mode of operation.

In some embodiments, the test object includes a grating structure and the information related to one or more under-resolved features of the test object includes one of: a grating (or other periodic structure) pitch, a grating depth.

In some embodiments, the test object includes one or more thin films, and the information related to one or more under-resolved features of the test object includes a thin film thickness.

In some embodiments, the test object includes a structure characterized by a critical dimension, and the information related to one or more under-resolved features of the test object includes the critical dimension.

In some embodiments, the interferometer system includes an interferometer configured to direct test light to a test surface and subsequently combine it with reference light to form an interference pattern, the test and reference light being derived from a common source, an electronic detector, and one or more optics configured to direct at least a portion of the combined light to the detector so that different regions of the detector correspond to different illumination angles of the test surface by the test light. The interferometer system is configured to operate in the first mode to direct the combined light to the detector so that the different regions of the detector correspond to the different illumination angles of the test surface by the test light and a second mode in which the different regions of the detector correspond to the different regions of the test surface illuminated by the test light to enable a profiling mode of operation.

In some embodiments, the apparatus includes a stage configured to adjust the position of the detector relative to the one or more optics to switch between the first and second modes of operation.

In some embodiments, the apparatus includes an electronic controller coupled to the detector stage and configured to adjustably cause the stage to switch between the first and second modes of operation.

In some embodiments, the one or more optics include a first set of one or more optics for operating in the first mode of operation and a second set of one or more optics for operating in the second mode of operation.

In some embodiments, the apparatus includes a multi-position optics holder supporting the first and second set of optics and configured to adjustably position one of the first and second sets and not the other of the first and second sets in the path of the combined light being directed to the detector to switch between the first and second modes.

In some embodiments, the multi-positioned lens holder is motorized, and the apparatus further includes an electronic controller coupled to the motorized multi-position optics holder to selectively cause the multi-position optics holder to switch between the first and second modes of operation.

In some embodiments, the apparatus includes a second set of one or more optics, a beam splitter positioned to direct a first portion of the combined to light to the first of optics and direct a second portion of the combined light to the second set of optics, and a second electronic detector, wherein the second set of optics is configured to direct the second portion of the combined light to the second electronic detector so that different regions of the second detector correspond to the different regions of the test surface illuminated by the test light.

In some embodiments, the interferometer includes a multi-position mount configured to support multiple objectives and position a selected objective in the path of input light from the common source, the multiple objectives including at least one interference objective.

In some embodiments, the multi-position mount is motorized, and the apparatus further includes an electronic controller coupled to the multi-position mount to selectively cause the mount to switch between objectives.

In some embodiments, the multiple objectives include two different interference objectives, only one of which includes a polarization optic.

In some embodiments, the multiple objectives include a non-interferometric objective, which when positioned in the path of the input light enables the apparatus to operate in a non-interferometric, microscope mode.

In some embodiments, the interferometer system includes a scanning interferometer. In some embodiments, the processor is configured to transform one or more of the interference signals from the first set of interferometry signals into a frequency domain to extract angularly resolved and wavelength-resolved information about the test surface based on the transformed signals. In some embodiments, the information includes reflectivity.

In another aspect, a method is disclosed which includes using an interferometry system in a first mode of operation to produce a first set of multiple interferometry signals corresponding to different illumination angles of a test object by test light, using the same interferometry system in a second mode produce a second set of multiple interferometry signals corresponding to different surface locations of a test object, comparing information derivable from the first set of multiple interferometry signals to information corresponding to multiple models of the test object to determine information related to one or more features of the test object; and outputting the information. In some embodiments the features include an under-resolved feature.

In some embodiments, the one or more under-resolved features of the test object correspond to one or more of a pitch, a modulation depth, and an element width for an under-resolved patterned structure on the test object.

In some embodiments, the one or more under-resolved features of the test object correspond to at least a modulation depth for an under-resolved patterned structure on the test object.

In some embodiments, at least some of the interferometry signals are derived from an illumination of the test object whose polarization is oriented with respect to elements of the under-resolved patterned structure. For example, in some embodiments, the polarization is a linear polarization aligned orthogonal to the length of the individual elements that define the under-resolved patterned structure In some embodiments, the one or more under-resolved features of the test object correspond to one or more of a height and a position of a step on the test object.

In some embodiments, the test object includes a patterned structure whose individual elements are obscured.

In some embodiments, the information related to the under-resolved feature corresponds to one or more of a modulation depth and an element width for the patterned structure.

In some embodiments, the models are generated computationally using rigorous coupled wave analysis.

In some embodiments, the models are generated empirically from test objects having known properties.

In some embodiments, the information about the under-resolved surface feature is outputted to a user.

In some embodiments, the information about the under-resolved surface feature is outputted to an automated process control system for semiconductor manufacturing.

In some embodiments, the interferometry signals are scanning interferometry signals. For example, in some embodiments, the scanning interferometry signal is produced by directing test light to interfere with reference light on a detector, and varying an optical path length difference from a common source to the detector between interfering portions of the test and reference light, wherein the test and reference light are derived from the common source, and wherein the scanning interferometry signal corresponds to an interference intensity measured by the detector as the optical path length difference is varied. Some embodiments also include producing the scanning interferometry signal.

Some embodiments, include transforming one or more of the interferometry signals from the first set of interferometry signals into a frequency domain to extract angularly resolved and wavelength-resolved information about the test surface based on the transformed signals.

In some embodiments, the interferometry system includes at least one electronic detector, and in the first mode different elements of the detector correspond to different illumination angles of the test surface by test light in the interferometry system.

In some embodiments, the information derivable from the first set of multiple interferometry signals includes the reflectivity of the test surface over the range of angles and wavelengths for one or more selected polarizations. In some embodiments, the reflectivity is a complex reflectivity.

In some embodiments, the information derivable from the first set of multiple interferometry signals includes the reflectivity of the test surface over the range of angles and wavelengths for unpolarized light. In some embodiments, the reflectivity is a complex reflectivity.

Some embodiments also includes imaging a pupil plane for test light directed to the test surface to the detector.

Some embodiments include determining information about the test object based on information derivable from the first and second sets of interferometry signals and outputting the information about the test object. For example, in some embodiments, the determining information about the test object includes using information derived in one mode of operation to assist in determining further information about the test object when using the other mode of operation.

In some embodiments, the determining information about the test object includes using the information related to the one or more under-resolved features of the test object determined in the first mode of operation to assist in determining further information about the test object when using the other mode of operation. For example, in some embodiments, the determining information about the test object includes deriving multiple models of the test object based on the information related to under-resolved features of the test object determined in the first mode of operation, comparing information derivable from the second set of multiple interferometry signals to information corresponding to the multiple models of the test object based on the information related to under-resolved features to determine further information related to the test object; outputting the further information related to the test object. In some embodiments, the further information about the test object includes a surface profile.

In another aspect, an apparatus is disclosed which includes an interferometer configured to direct test light to a test object and subsequently combine it with reference light to form an interference pattern, the test and reference light being derived from a common source, an electronic detector, one or more optics configured to direct at least a portion of the combined light to the detector so that different regions of the detector correspond to different illumination angles of the test object by the test light and an electronic processor coupled to the detector. The electronic processor is configured to store calibration information about the optical properties of the interferometer, process information measured by the detector to determine information related to an under-resolved feature of the test object based on the calibration data and based on a comparison of information derived from the information measured by the detector to information corresponding to multiple models of the test object; and output the information related to a feature of the test object. In some embodiments the features include an under-resolved feature.

In some embodiments, the electronic processor is configured to extract angularly resolved reflectivity information about the test object from the detector measurement, and wherein the information derived from the information measured by the detector is the angularly resolved reflectivity.

In some embodiments, the apparatus includes a translation stage configured to adjust the relative optical path length between the test and reference light when they form the interference pattern, wherein the electronic processor is configured to analyze an interference intensity signal measured at each of multiple locations across the detector and produced by scanning the translation stage. In some embodiments, the electronic processor is configured to determine the correspondence between the different regions of the detector and the different illumination angles of the test surface by the test light based on the frequency of the intensity signal at different locations on the detector.

In some embodiments, the electronic processor is configured to extract angularly resolved and wavelength-resolved information about the test surface based on the intensity signals measured across the detector. In some embodiments, the electronic processor is configured to transform the interference signal at different locations of the detector into a frequency domain to extract the angularly resolved and wavelength-resolved information. For example, in some embodiments, the interferometer includes one or more polarization elements positioned to adjust the polarization content of the interference pattern measured by the detector, and wherein the electronic processor is configured to extract angularly resolved, wavelength-resolved, and polarization-resolved information about the test surface based on the intensity signal measured across the detector. In some embodiments, the angularly resolved, wavelength-resolved, and polarization-resolved information is related to the reflectivity of the test surface.

In another aspect, an interferometry method is disclosed which includes directing test light to a test surface of a test object over a range of illumination angles; subsequently combining the test light with reference light to form an interference pattern, wherein the test and reference light are derived from a common source, wherein the test surface has known reflection properties, and directing at least a portion of the combined light to a multi-element detector so that different elements of the detector correspond to different illumination angles of the test surface by the test light. The method also includes measuring interferometry signals corresponding to the different elements of the detector, calibrating reflection parameters of an interferometer used to direct the test light and combine it with the reference light based on the interferometry signals measured at different detector elements and the known reflection parameters of the test surface, comparing information derivable from the interferometry signals to information corresponding to multiple models of the test object to determine information related to one or more features of the test object; and outputting the information. In some embodiments, the features include an under-resolved feature.

In some embodiments, the models are based on the calibrated reflection parameters.

In some embodiments, the method also includes repeating the directing, measuring, and calibrating steps with a second test surface having known reflection properties and further calibrating reflection parameters of the interferometer based on signals measured at the different detector elements and the known reflection parameters of the test surfaces.

In another aspect, an interferometry method is disclosed which includes directing test light to a test surface of a test object over a range of illumination angles; subsequently combining the test light with reference light to form an interference pattern, wherein the test and reference light are derived from a common source, and directing at least a portion of the combined light to a multi-element detector so that different elements of the detector correspond to different illumination angles of the test surface by the test light, wherein the test surface has known reflection properties. The method also includes measuring interferometry signals corresponding to the different elements of the detector as a function of varying an optical path length difference between the test and reference light, determining calibration information based on the interferometry signals, comparing information derivable from the interferometry signals to information corresponding to multiple models of the test object to determine information related to one or more features of the test object, and outputting the information. In some embodiments the features include an under-resolved feature.

In some embodiments, the determining calibration information includes determining the location of an optical axis for the combined light on the detector based on the frequency of the interference signal at different detector elements.

In some embodiments, the determining calibration information includes determining the rate at which the optical path length difference is varied by based on the frequency of the interference signal at different detector elements.

In some embodiments, the models are based on the calibration information.

In another aspect, an apparatus is disclosed including an interferometer including an interference objective with a pupil plane, a light source, an electronic detector, one or more optics configured to direct at least a portion of the combined light to the detector so that different regions of the detector correspond to different illumination angles of the test surface by the test light, and an electronic processor coupled to the detector. The light source and the interferometer are configured to provide illumination of the pupil plan which is not Koehler illumination. The electronic processor is configured to process information measured by the detector to determine information related to one or more features of the test object based on a comparison between data based on the information measured by the detector and data based on multiple models for the test object. In some embodiments, the features include an under-resolved feature.

In some embodiments, the illumination is critical illumination.

In some embodiments, the interferometer and light source are configured to provide light with a mutual coherence function that is greater than zero for one or more pairs of spatially separated points on the pupil plane.

In some embodiments, the interferometer and light source are configured to direct light from a source to the pupil plane such that the source is not imaged at the pupil plane.

In another aspect, a method is disclosed including providing illumination of a pupil plane of an interferometer objective to form test light, thereby providing test light and reference light in the interferometer objective, wherein the illumination is not Koehler illumination, directing the test light to a test surface of a test object over a range of illumination angles; subsequently combining the test light with reference light to form an interference pattern, wherein the test and reference light are derived from a common source, directing at least a portion of the combined light to a multi-element detector so that different elements of the detector correspond to different illumination angles of the test surface by the test light, measuring interferometry signals corresponding to the different elements of the detector, comparing information derivable from the interferometry signals to information corresponding to multiple models of the test object to determine information related to one or more features of the test object and outputting the information. In some embodiments, the features include an under-resolved feature.

In some embodiments, the providing illumination includes providing critical illumination.

In some embodiments, the providing illumination includes providing light with a mutual coherence function that is greater than zero for one or more pairs of spatially separated points on the pupil plane.

In some embodiments, the providing illumination includes directing light from a source to the pupil plane such that the source is not imaged at the pupil plane.

In general, in another aspect, the invention features a method, including obtaining test data using an interferometer, the test data including information about the reflection of test light from a test object for different angles of incidence of the test light on the test object, different wavelengths of test light, and different azimuthal angles of the test light on the test surface, where the test data satisfies a phase relationship which relates test data at different wavelengths and incident angles, and the phase relationship depends on a position of the test object with respect to the interferometer. The method includes providing one or more sets of model data, each model data set characterizing the reflection of light from a corresponding model object, comparing the test data to one or more sets of the model data to select a matching model data set, wherein the matching model data set satisfies the phase relationship, and determining information about one or more under-resolved features of the test object based on the model test object corresponding to the selected model data set.

Implementations of the method can include one or more of the following features and/or features of other aspects. For example, the phase relationship can depend on a distance of the test object from the interferometer. The phase relationship can require:

$$\frac{\lambda_1}{\cos\alpha_1}\arg\left(\frac{z(\alpha_1, \lambda_1, \theta_1)}{R(\alpha_1, \lambda_1, \theta_1)}\right) = \frac{\lambda_2}{\cos\alpha_2}\arg\left(\frac{z(\alpha_2, \lambda_2, \theta_2)}{R(\alpha_2, \lambda_2, \theta_2)}\right),$$

where $\lambda_1$ and $\lambda_2$ are different wavelengths of the test light, $\alpha_1$ and $\alpha_2$ are different incident angles of the test light, $\theta_1$ and $\theta_2$ are different azimuthal angles of the test light, z is a quantity derived from the test data at $\alpha_i$, $\lambda_i$, and $\theta_i$, and R is a modeled complex reflectivity at $\alpha_i$, $\lambda_i$, and $\theta_i$, where i=1,2.

In some embodiments, the interferometer is configured to image a pupil plane of the interferometer onto a multi-element detector so that different regions of the detector correspond to different incident angles of the test light on the test object.

Obtaining the test data can include transforming one or more interference signals measured using the interferometer into a frequency domain.

The model data can include a complex reflectivity value calculated for different incident angles $\alpha$, wavelengths $\lambda$, and azimuthal angles $\theta$.

Comparing the test data and the model data can include solving a merit function related to a difference between the test data and model data for different incident angles $\alpha$, wavelengths $\lambda$, and azimuthal angles $\theta$. The merit function can be parameterized by at least one structural parameter of the model objects and a scalar, $\Delta h$, related to the position of the test object with respect to the interferometer. The at least one structural parameter can be a modulation depth or an element width of a patterned structure. The patterned structure can be a periodic structure (e.g., a grating).

Different model data sets can correspond to model objects having different under-resolved features. The model data can be generated computationally using rigorous coupled wave analysis. The sets of modeled data can be determined prior to the obtaining the test data.

In some embodiments, a further set of model data is generated computationally after comparing a first set of modeled data to the test data. Comparing the test data and the model data sets can include performing an iterative regression by generating a new set of modeled data based on a prior comparison of a model data set to the test data. For instance, an optimizing algorithm such as a Levenberg-Marquardt solver can be used to perform the regression and optimize model parameters to minimize a difference between model and test data.

In general, in another aspect, the invention features an apparatus that includes an interferometer configured to direct test light to a test object and subsequently combine it with reference light to form an interference pattern, the test and reference light being derived from a common source, an electronic detector, one or more optics configured to direct at least a portion of the combined light to the detector so that different regions of the detector correspond to different illumination angles of the test object by the test light, and an electronic processor coupled to the detector. The electronic processor is configured to: i) obtain test data from the interferometer, the test data including information about the reflection of test light from the test object for different angles of incidence of the test light on the test object, different wavelengths of test light, and different azimuthal angles of the test light on the test surface, where the test data satisfies a phase relationship which relates test data at different wavelengths and incident angles, and the phase relationship depends on a position of the test object with respect to the interferometer; ii) compare the test data to one or more sets of the model data to select a matching model data set, where each model data set characterizing the reflection of light from a corresponding model object and the matching model data set satisfies the phase relationship; and iii) determine information about one or more under-resolved features of the test object based on the model test object corresponding to the selected model data set. Embodiments of the apparatus can include one or more features of other aspects.

Embodiments may include any of the features or characteristics found in the various embodiments described above.

As used herein, "light" and "optical" does not only refer to visible electromagnetic radiation; rather such terms include electromagnetic radiation in any of the ultraviolet, visible, near-infrared, and infrared spectral regions.

Unless otherwise defined, all technical and scientific terms used herein have the same meaning as commonly understood by one of ordinary skill in the art to which this disclosure belongs. In case of conflict with any document incorporated by reference, the present disclosure controls.

Other features are described in the following detailed description.

BRIEF DESCRIPTION OF THE DRAWINGS

FIG. 6b shows the results of the characterization of the grating illustrated in FIG. 6a.

Like reference numerals in different drawings refer to common elements.

DETAILED DESCRIPTION

Figure 1:
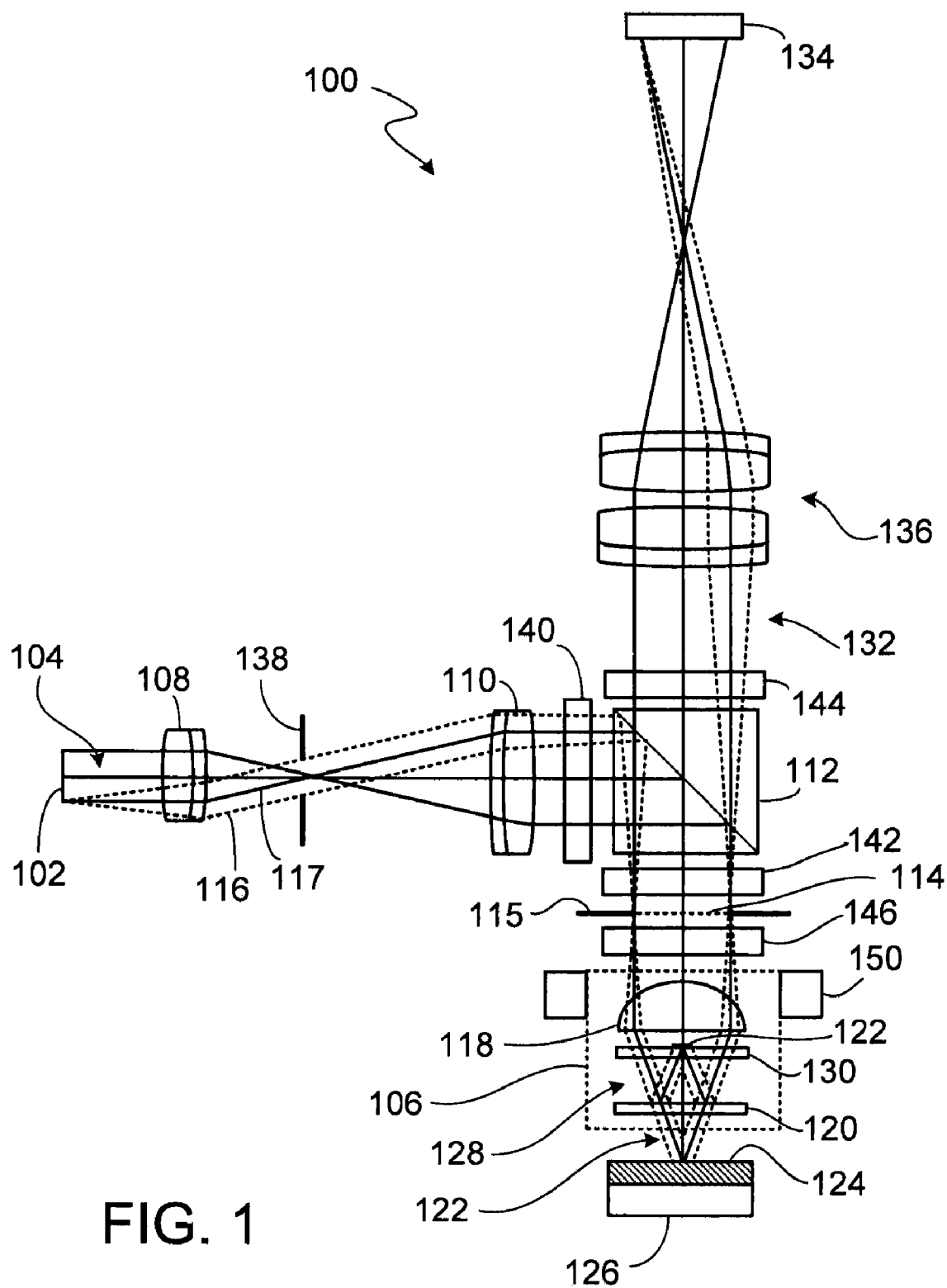
FIG. 1 is a schematic diagram of an interferometry system 100 configured to operate in an ellipsometry mode.

FIG. 1 is a schematic diagram of an interferometry system 100, of the type described in US Patent Publication No. 2006-0158659-A1 "INTERFEROMETER FOR DETERMINING CHARACTERISTICS OF AN OBJECT SURFACE" by Xavier Colonna de Lega et. al., US Patent Publication No. 2006-0158658-A "INTERFEROMETER WITH MULTIPLE MODES OF OPERATION FOR DETERMINING CHARACTERISTICS OF AN OBJECT SURFACE", by Xavier Colonna de Lega et. al., and US Patent Publication No. 2006-0158657"A INTERFEROMETER FOR DETERMINING CHARACTERISTICS OF AN OBJECT SURFACE, INCLUDING PROCESSING AND CALIBRATION" by Xavier Colonna de Lega et. al., each of which is in incorporated herein by reference.

A spatially extended source 102 directs input light 104 to an interference objective 106 via relay optics 108 and 110 and beam splitter 112. The relay optics 108 and 110 image input light 104 from spatially extended source 102 to an aperture stop 115 and corresponding pupil plane 114 of the interference objective 106 (as shown by the dotted marginal rays 116 and solid chief rays 117).

In the embodiment of FIG. 1, interference objective 106 is of the Mirau-type, including an objective lens 118, beam splitter 120, and reference surface 122. Beam splitter 120 separates input light 104 into test light 122, which is directed to a test surface 124 of a test object 126, and reference light 128, which reflects from reference surface 122. Objective lens 118 focuses the test and reference light to the test and reference surfaces, respectively. The reference optic 130 supporting reference surface 122 is coated to be reflective only for the focused reference light, so that the majority of the input light passes through the reference optic before being split by beam splitter 120.

After reflecting from the test and reference surfaces, the test and reference light are recombined by beam splitter 120 to form combined light 132, which is transmitted by beam splitter 112 and relay lens 136 to form an optical interference pattern on an electronic detector 134 (for example, a multi-element CCD or CMOS detector). The intensity profile of the optical interference pattern across the detector is measured by different elements of the detector and stored in an electronic processor (not shown) for analysis. Unlike a conventional profiling interferometer in which the test surface is imaged onto the detector, in the present embodiment, relay lens 136 (e.g., a Bertrand lens) images different points on the pupil plane 114 to corresponding points on detector 134 (again as illustrating by dotted marginal rays 116 and solid chief rays 117).

Because each source point illuminating pupil plane 114 creates a plane wave front for test light 122 illuminating test surface 124, the radial location of the source point in pupil plane 114 defines the angle of incidence of this illumination bundle with respect to the object normal. Thus, all source points located at a given distance from the optical axis correspond to a fixed angle of incidence, by which objective lens 118 focuses test light 122 to test surface 124. A field stop 138 positioned between relay optic 108 and 110 defines the area of test surface 124 illuminated by test light 122. After reflection from the test and reference surfaces, combined light 132 forms a secondary image of the source at pupil plane 114 of the objective lens. Because the combined light on the pupil plane is then re-imaged by relay lens 136 onto detector 134, the different elements of the detector 134 correspond to the different illumination angles of test light 122 on test surface 124.

In some embodiments, polarization elements 140, 142, 144, and 146 are optionally included to define the polarization state of the test and reference light being directed to the respective test and reference surfaces, and that of the combined light being directed to the detector. Depending on the embodiment, each polarization element can be a polarizer (e.g., a linear polarizer), a retardation plate (e.g., a half or quarter wave plate), or a similar optic that affects the polarization state of an incident beam. Furthermore, in some embodiments, one or more of the polarization elements can be absent. In some embodiment these elements are adjustable, for instance mounted on a rotation mount, and even motorized under electronic control of the system. Moreover, depending on the embodiment, beam splitter 112 can be polarizing beam splitter or a non-polarizing beam splitter. In general, because of the presence of polarization elements 140, 142 and/or 146, the state of polarization of test light 122 at test surface 124 can be a function of the azimuthal position of the light in pupil plane 114.

In the presently described embodiment, source 102 provides illumination over a broad band of wavelengths (e.g., an emission spectrum having a full-width, half-maximum of more than 50 nm, or preferably, even more than 100 nm). For example, source 102 can be a white light emitting diode (LED), a filament of a halogen bulb, an arc lamp such as a Xenon arc lamp or a so-called supercontinuum source that uses non-linear effects in optical materials to generate very broad source spectra (>200 nm). The broad band of wavelengths corresponds to a limited coherence length.

As in conventional scanning interferometer, a translation stage 150 adjusts the relative optic path length between the test and reference light to produce an optical interference signal at each of the detector elements. For example, in the embodiment of the FIG. 1, translation stage 150 is a piezoelectric transducer coupled to interference objective 106 to adjust the distance between the test surface and the interference objective, and thereby vary the relative optical path length between the test and reference light at the detector. The optical interference signals are recorded and processed by computer 151.

Figure 2:
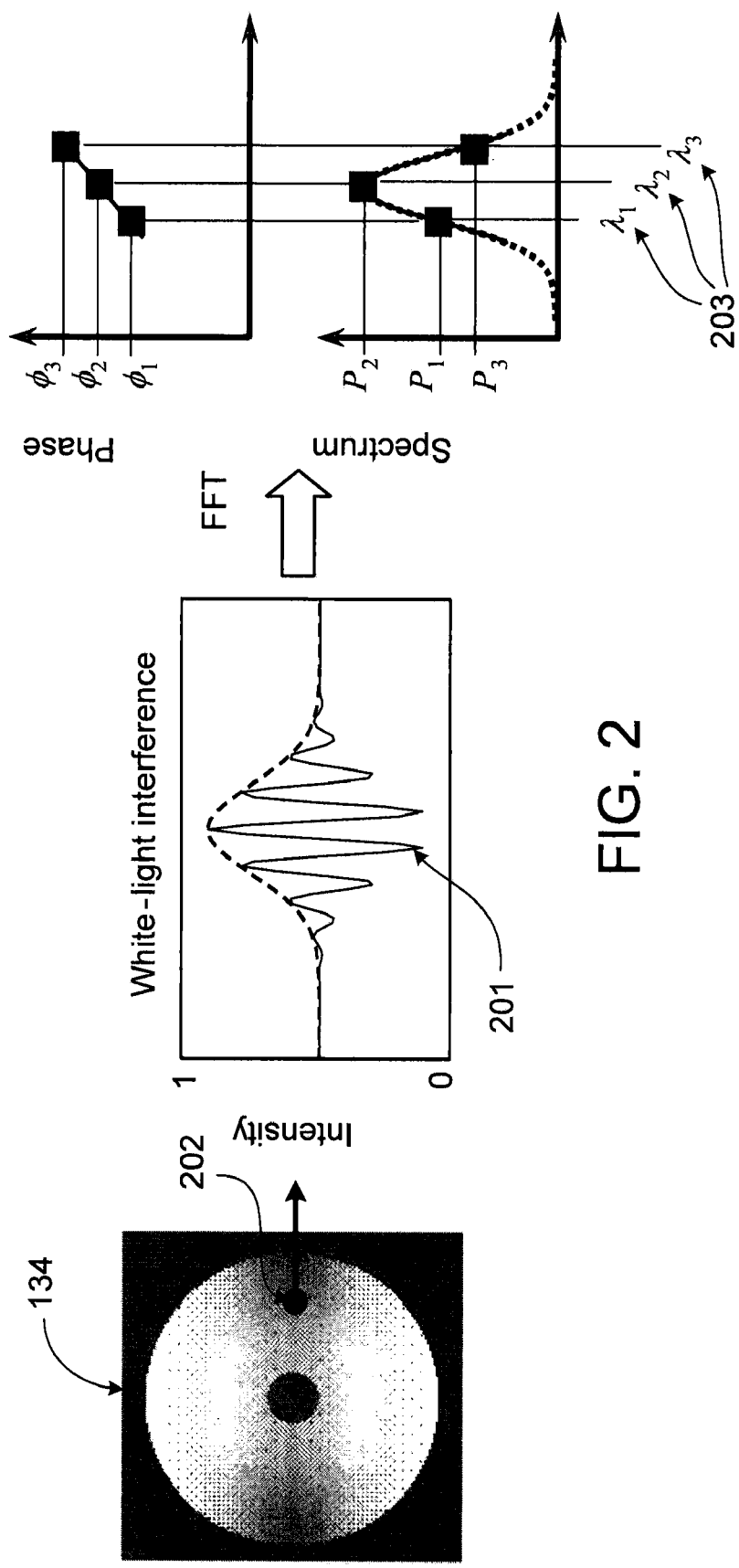
FIG. 2 is a schematic illustrating the acquisition and processing of a typical interference signal detected by interferometry system 100.

FIG. 2 shows an exemplary interference signal 201 measured by detector element 202 of detector 134 as translation stage 150 varies the relative optical path length between the test and reference light. The interference signal 201 is modulated by a contrast envelope corresponding to the coherence length of the source. In some embodiments, the reference surface is positioned in the interferometer so that a zero optical path length difference between the test and reference light corresponds to a position of the test surface that is in focus with respect to objective lens 118. Thus, maximum contrast is generally observed when the test surface is in this in-focus position relative to the interference objective. A measurement is performed by scanning the translation stage 150 over a range larger than the coherence length so that the contrast envelope is captured in a sequence of intensity patterns measured at detector 134.

The interference signal measured at each detector element is analyzed by the electronic processor, which electronically coupled to both detector 134 and translation stage 150. In the presently described embodiment, the electronic processor transforms the interference signal into the frequency domain using, for example, a Fourier Transform or Fast Fourier Transform, to extract the phase 202 and amplitude 203 information for the different wavelength components of the light source. Preferably, the source spectrum is broad so that many independent spectral components can be calculated with this procedure. The amplitude and phase data relate directly to the complex reflectivity of the test surface, which can be analyzed to determine information about the test object. In some embodiments, the electronic processor uses information from a separate calibration to correct the measurement for the reflectivity of the reference mirror and other optical characteristics of the interferometer. Because of the arrangement of interferometry system 100, each detector element of electronic detector 134 provides reflectivity measurements at a multiplicity of wavelengths produced by source 102, for a specific angle of incidence and polarization state (according to the orientations of polarization elements 140, 142, 144 and/or 146). The collection of detector elements thus covers a range of angles of incidence, polarization states and wavelengths, which increases the ability of the instrument to properly characterize unknown optical structures.

Figure 3:
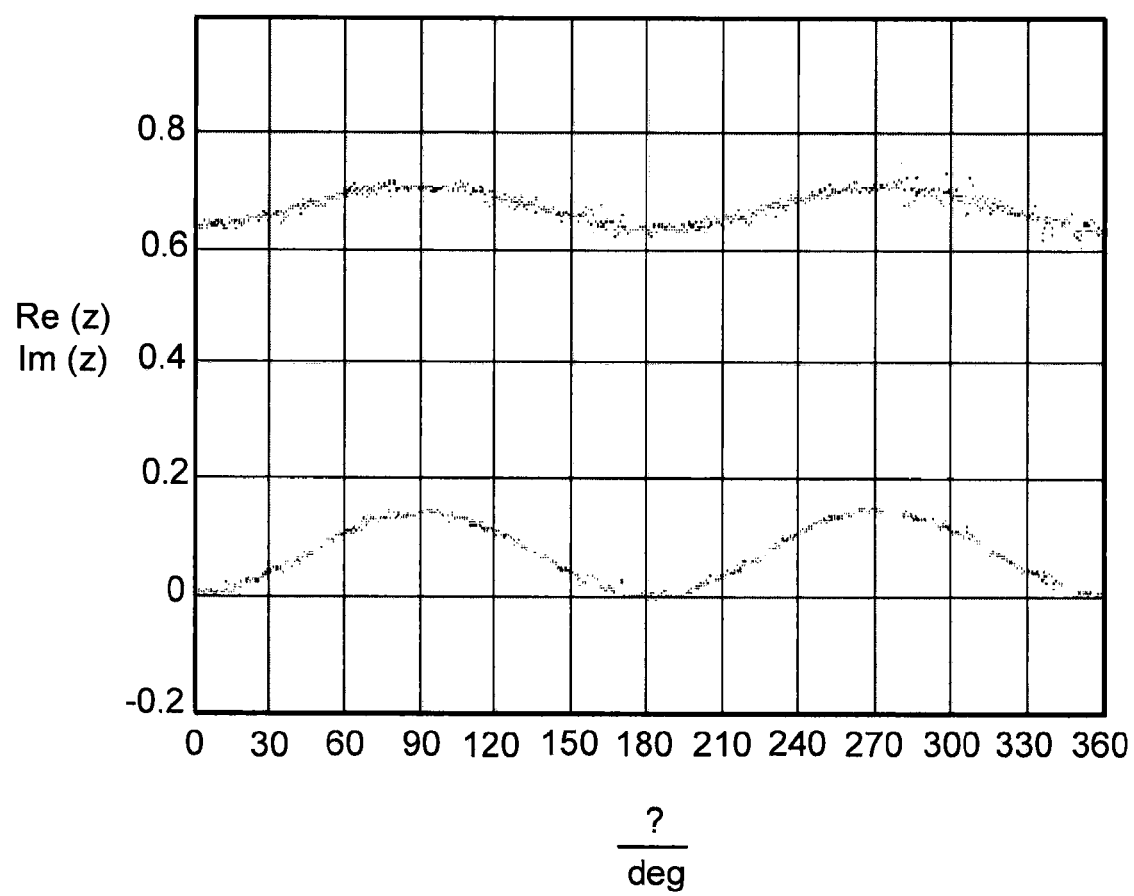
FIG. 3 shows a plot of experimentally derived complex reflectivity.

FIG. 3 shows an exemplary plot of experimentally derived complex reflectivity measured using the above described techniques. The complex reflectivity coefficient is plotted for a selected angle of incidence (43 degrees) and a selected wavelength (576 nm) as a function of azimuth angle for, in this case, a 675-nm thick silicon dioxide monolayer film on a silicon substrate. The top curve is the real component of the complex reflectivity and the bottom curve is the imaginary component.

Figure 4:
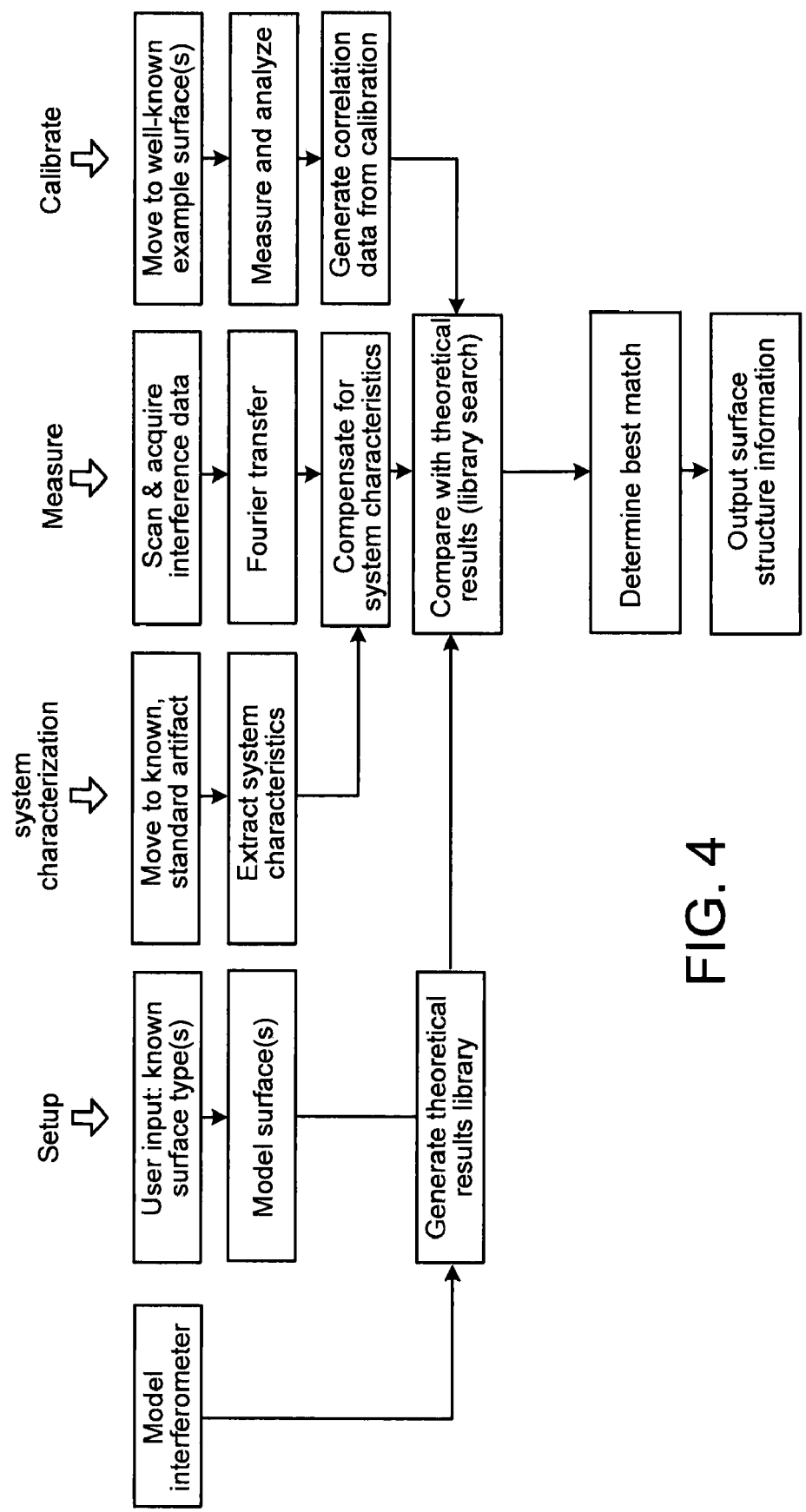
FIG. 4 is a flow chart describing a characterization process.

FIG. 4 shows a flowchart describing the characterization process. As described above, a computer records an interference intensity signal for each of multiple detector elements. Next, after storing interference intensity signal as a function of scan position for each of the different detector elements, the computer performs a transform (e.g., a Fourier Transform or Fast Fourier Transform) to generate a frequency-domain spectrum of the signal. The spectrum contains complex reflectivity information at a multiplicity of wavelengths produced by source 102, for a specific angle of incidence and polarization state of the illuminating light.

In a separate step, the computer generates a library of theoretical predictions for interferometry data (e.g., the frequency-domain spectra) for a range of surface features and a model for the interferometer. As an alternative, the prediction library may be generated empirically, using sample artifacts. As another alternative, the library may use information from prior supplemental measurements of the object surface provided by other instruments, for example an ellipsometer, and any other input from a user regarding known properties of the object surface, so as to reduce the number of unknown surface parameters. Any of these techniques for library creation, theoretical modeling, empirical data, or theory augmented by supplemental measurements, may be expanded by interpolation to generate intermediate values, either as part of the library creation or in real time during a library search.

A proper physical model of the optics can be very elaborate, taking into account the partial coherence of the light source, polarization mixing in the interferometer, the imaging properties of high-NA objectives, and the interaction of electric field vectors at high angles of incidence and in the presence of discontinuous surface features.

For example, to rigorously predict the interferometer signal from a given structure requires solving Maxwell's Equations for that structure. White light interferometry requires a sufficiently dense set of wavelengths covering the bandwidth of the illumination. There are many approaches to solving Maxwell's Equations in 2D. In 2D one particularly simple approach is based on the Rayleigh Hypothesis. In this approach the structure is treated as a thin film stack but with the interfaces between each layer in the stack having a specific topography. The Rayleigh Hypothesis states that within each layer the electromagnetic field can be expanded in upward and downward propagating plane waves and the solution can be generated by choosing the coefficients so that the electromagnetic field satisfies the standard boundary conditions at the interfaces. This approach is easy to implement, relatively fast and it generates the full optical transfer function or scattering matrix of the surface at one wavelength and for one polarization in a single computation. A limitation is that it generates valid solutions only in cases where the topography of each interface covers less than roughly half the wavelength in the layers bounding the interface. Hence, high index materials such as silicon restrict the topography at visible wavelengths to be much less than 100 nm.

3D modeling techniques include Finite Difference Time Domain (FDTD), Finite Element and rigorous coupled-wave analysis (RCWA). See, e.g., M. G. Moharam and T. K. Gaylord, "Diffraction analysis of dielectric surface-relief gratings." J. Opt. Soc. Am., 72, 1385-1392, (1982), and M. Totzeck, "Numerical simulation of high-NA quantitative polarization microscopy and corresponding near-fields", Optik, 112 (2001) 381-390. Moreover, the Institute of Technical Optics (ITO) at the University of Stuttgart has developed software for performing RCWA called Microsim, based on the work of M. Totzek. These techniques are powerful although often limited to small volumes, i.e., a few wavelengths on a side, to keep both the memory requirements and the runtimes reasonable. Nonetheless, because, in some embodiments, such techniques can be used in advance to generate suitable libraries, extensive computation time used to generate the libraries does not hinder in-process application of the techniques disclosed herein.

In a next step, the experimental data is compared to the prediction library by means of, for example, a library search. For example, in some embodiments, the library contains predicted signals for a diffraction grating that is unresolved in a conventional microscope at visible wavelengths. The library contains predicted signals for structures with a range of pitch, depth and film structure.

In another example, in embodiments for measuring more complex features such as semiconductor test patterns, the expected signals are modeled using, for example, RCWA or related generalized solution techniques for Maxwell's equations. The library contains predicted signals for range of possible shape factors of the structure.

The analysis may also include a system characterization, which includes, e.g. measuring one or more reference artifacts having a known surface structure and surface topography, so as to determine parameters such as system wavefront error, dispersion, and efficiency that may not be included in the theoretical model.

Furthermore, the analysis may include an overall calibration, which includes e.g., measuring one or more reference artifacts to determine the correlation between measured surface parameters, such as film thickness as determined by the library search, and the values for these parameters as determined independently, e.g. by ellipsometric analysis.

Based on the comparison of the experimental data to the prediction library, the computer identifies the surface model corresponding to the best match. It may then displays (e.g., numerically or graphically) or transmits surface structure information (e.g., pitch, depth, film structure, or shape factors) corresponding to the best match to the user or to a host system for further analysis or for data storage. In some cases, the library search and data collection can be performed iteratively to further improve the results.

As discussed above, during processing of the interferometry signals, the computer performs a transform, such as a Fourier transform on the interferometry signals. Without wishing to be bound by theory, the application of a Fourier transform to the interference signal measured at individual pupil locations yields a measured spectral component $Z(\alpha, \lambda, \theta)$ as a function of angle of incidence $\alpha$, wavelength $\lambda$ and azimuthal location $\theta$:

$$Z(\alpha, \lambda, \theta) = I(\alpha, \lambda, \theta)\exp\left(-i\frac{4\pi}{\lambda}h\cos\alpha\right)R(\alpha, \lambda, \theta) \quad (1)$$

where h is an unknown height representing the location of the object surface within the OPD scan used to collect interference data. The mathematical formalism of the relationship shown in Eq. (1) is presented in U.S. Patent Application Pub. No. 2006-0158659-A1, filed on Jan. 19, 2006, the entire contents of which is incorporated herein by reference. As discussed in US 2006-0158659-A1, $I(\alpha, \lambda, \theta)$ is an object-independent complex-valued function describing phase and intensity variations across the pupil of the interferometer. This function effectively characterizes intrinsic attributes of the interferometer and optical system. Finally, the complex-valued function $R(\alpha, \lambda, \theta)$ represents the contribution of the object surface to the interference signal. For example, for a system where the illumination light is linearly polarized in the plane of the pupil and where a parallel analyzer is placed in the imaging leg this function takes the following form when the object is an isotropic un-patterned film stack:

$$R(\alpha,\lambda,\theta)=\cos(\theta)^2 rp(\alpha,\lambda)-\sin(\theta)^2 \tau(\alpha,\lambda) rs(\alpha,\lambda) \qquad (2)$$

where rp, rs are the Fresnel reflection coefficients for the film stack, $\theta$ is the azimuthal angle measured with respect to the polarizer axis and $\tau(\alpha, \lambda)$ is a complex-valued function capturing relevant attributes of the interferometer.

In the case of a scattering structure, the function $R(\alpha, \lambda, \theta)$ does not necessarily have an analytical form and its value will ultimately have to be modeled using for example RCWA code. We denote $R(\alpha, \lambda, \theta, M)$ such a model function for which the list of model parameters (e.g., film thickness, optical properties, structure geometry, etc) is represented by the variable M. These are effectively the end product of the measurement process.

As described in US 2006-0158659-A1, a system characterization procedure using known samples can be used to provide estimates of $I(\alpha, \lambda, \theta)$ and $\tau(\alpha, \lambda)$. Measurement of a sample to be characterized provides experimental data that theoretically take the form shown in Eq.(1). Assuming that the spectral distribution of the light source and average light level have not changed between characterization and measurement of the sample, one can derive a new quantity:

$$z(\alpha, \lambda, \theta) = \frac{Z(\alpha, \lambda, \theta)}{I(\alpha, \lambda, \theta)\exp\left(-i\frac{4\pi}{\lambda}h_0\cos\alpha\right)} = \exp\left(i\frac{4\pi}{\lambda}\Delta h\cos\alpha\right)R(\alpha, \lambda, \theta) \qquad (3)$$

where $\Delta h$ is an unknown height value related to the unknown heights of the samples used for system characterization and the unknown height of the measured sample.

For a given measurement it is possible to group the data collected at the pupil in sets of data rings that capture ranges of azimuthal positions for given pairs $(\alpha, \lambda)$. Each ring can be processed independently of the others. For instance, the magnitude of the measured values $z(\alpha, \lambda, \theta)$ is equal to the magnitude of the unknown quantity $R(\alpha, \lambda, \theta)$. Similarly, the ratios of ring components at different azimuthal locations provide both amplitude ratios and phase differences that are now independent of $\Delta h$. We have thus the following relationships:

$$|z(\alpha, \lambda, \theta)| = |R(\alpha, \lambda, \theta)| \qquad (4)$$

$$\arg\left(\frac{z(\alpha, \lambda, \theta_1)}{z(\alpha, \lambda, \theta_2)}\right) = \arg\left(\frac{R(\alpha, \lambda, \theta_1)}{R(\alpha, \lambda, \theta_2)}\right)$$

where the arg( ) function returns the argument of a complex number.

These conditions can form the basis for an optimization process that refines the parameters, M, of the model used to calculate the values of $R(\alpha, \lambda, \theta)$ and match them to the experimental data $z(\alpha, \lambda, \theta)$. For example, in the specific case where Eq.(2) is valid, the above conditions become:

$$|z(\alpha, \lambda, \theta = 0)| = |rp(\alpha, \lambda)| \qquad (5)$$

$$\left|z\left(\alpha, \lambda, \theta = \frac{\pi}{2}\right)\right| = |\tau(\alpha, \lambda)||rs(\alpha, \lambda)|$$

$$-\frac{z(\alpha, \lambda, \theta = 0)}{\tau(\alpha, \lambda)z\left(\alpha, \lambda, \theta = \frac{\pi}{2}\right)} = \frac{rp(\alpha, \lambda)}{rs(\alpha, \lambda)} = \tan\psi \exp i\Delta$$

In this case the experimental ring data provide the ellipsometric parameters $\psi$ and $\Delta$ as well as estimates of the magnitude of the complex reflectivity coefficients. Note that in practice these parameters can be advantageously determined by fitting a model function to the entire ring data instead of using only specific azimuthal locations.

The scheme presented so far allows optimizing the parameters of a model of the object structure. This process can be applied simultaneously to multiple rings (i.e., multiple wavelengths and angles of incidence), for example, by minimizing a merit function of the form:

$$\chi^2(M, \varphi) = \sum_i \frac{1}{\sigma_i^2}|z(\alpha_i, \lambda_i, \theta_i) - R(\alpha_i, \lambda_i, \theta_i, M)\exp(i\varphi(\alpha_i, \lambda_i))|^2 \qquad (6)$$

where $\sigma_i$ is the standard deviation of the uncertainty associated to a given measurement point $z(\alpha_i, \lambda_i, \theta_i)$ and where $\phi(\alpha_i, \lambda_i)$ is an arbitrary phase offset that is effectively optimized independently for each ring of data.

In some embodiments, additional information can be applied to the optimization process. Indeed, the use of an interferometer to collect the data creates a global phase relationship between the different rings of data. This relationship can be expressed as:

$$4\pi\Delta h = \frac{\lambda_1}{\cos\alpha_1}\arg\left(\frac{z(\alpha_1, \lambda_1, \theta_1)}{R(\alpha_1, \lambda_1, \theta_1)}\right) = \ldots = \frac{\lambda_i}{\cos\alpha_i}\arg\left(\frac{z(\alpha_i, \lambda_i, \theta_i)}{R(\alpha_i, \lambda_i, \theta_i)}\right) \qquad (7)$$

In other words, the global phase relationship can be used to constrain model data that is being compared to experimental data, differentiating between model data that otherwise satisfy the relationships expressed in Eq. (4). Accordingly, comparing model data and test data using the global phase relationship can provide more robust and accurate results that using the relationships of Eq. (4) alone.

In embodiments, combining the ring-specific conditions defined by Eq.(4) and the global phase condition defined by Eq.(7) can be accomplished, for example, by defining a merit function of the form:

$$\chi^2(M, \Delta h) = \qquad (8)$$

$$\sum_i \frac{1}{\sigma_i^2}\left|z(\alpha_i, \lambda_i, \theta_i) - R(\alpha_i, \lambda_i, \theta_i, M)\exp\left(i\frac{4\pi}{\lambda_i}\Delta h\cos\alpha_i\right)\right|^2$$

where $\Delta h$ is now a single scalar value. There is no equivalent relationship to Eq. (7) between measurements at different wavelengths or angles of incidence for optical tools such as reflectometers, ellipsometers or polarimeters, when used to characterize unresolved scattering structures.

In some embodiments, the approach described above can be extended to the case where the light level or spectral distribution of the light source has changed between the time of system characterization and actual measurement on an unknown sample. The simplest model consists in assuming that the illumination light level changed uniformly and is independent of wavelength, angle of incidence, azimuthal location, etc. Depending on the mechanism used in a given system to adjust the source illumination level a more complicated model might be required that would for instance take into account spectral variation with source intensity. The more general case can provide the freedom to optimize the light level on a ring basis.

Figure 5:
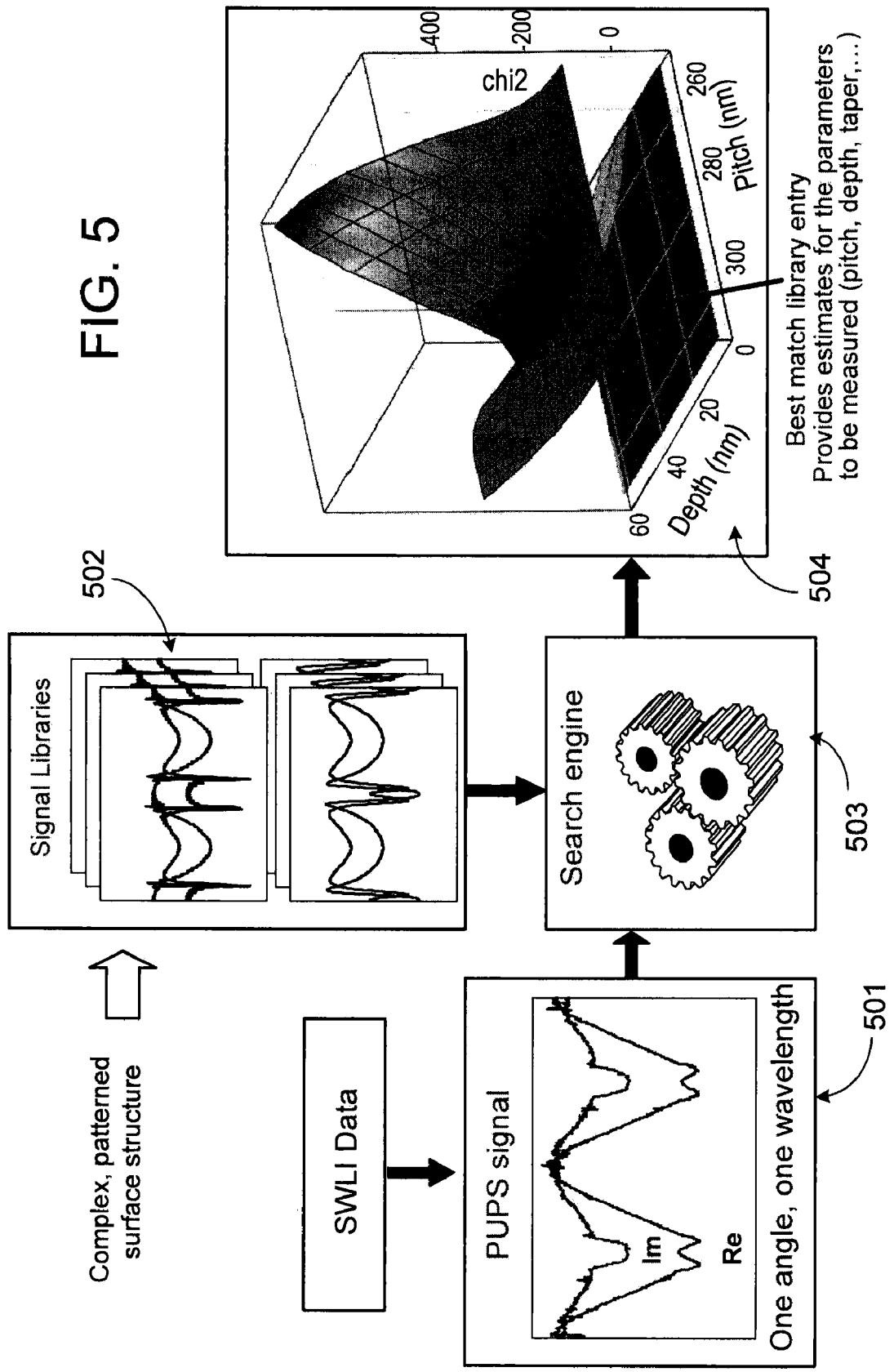
FIG. 5 is an illustration of data processing using a library search technique.

FIG. 5 illustrates an example of data processing using a library search technique. The azimuthally-resolved signal 501 for a single incident angle defined by a specific radial position in the pupil image is compared with the predicted signals 502 over a range of possible feature structure definitions, using, e.g., a least-squares technique. This comparison is repeated over a range of incident angles and wavelengths (not shown) to determine the best fit 503 of experimental data to theoretical predictions and thus to a specific features shape and dimension. When the best match library entry provides estimates for various parameters of the surface structure to be measured (e.g., pitch, depth, taper, etc.). Although a two dimensional parameter space is shown, the parameter space may, in general, have a higher dimension.

Figure 6A:
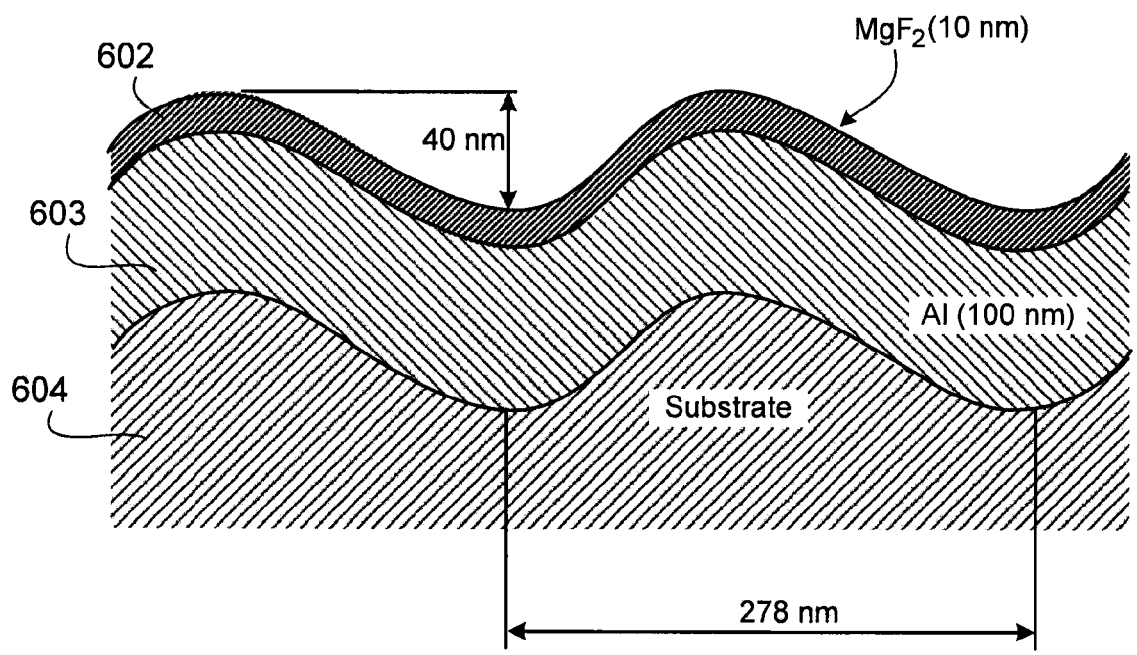
FIG. 6a is a schematic of a sinusoidal diffraction grating.

FIG. 6a illustrates the use of the above described techniques to determine the pitch, depth and film structure of a diffraction grating 601 that is unresolved in a conventional microscope at visible wavelengths. The surface structure to be measured consists of a grating with a layer of $MgF_2$ 602 on a layer of aluminum 603 on substrate 604. The grating has a nominal pitch of 278 nm and a nominal depth of 45 nm. A library of predicted signals is provided which includes entries for grating structures with a range of film thicknesses, grating pitches, and grating depths.

Figure 6B:
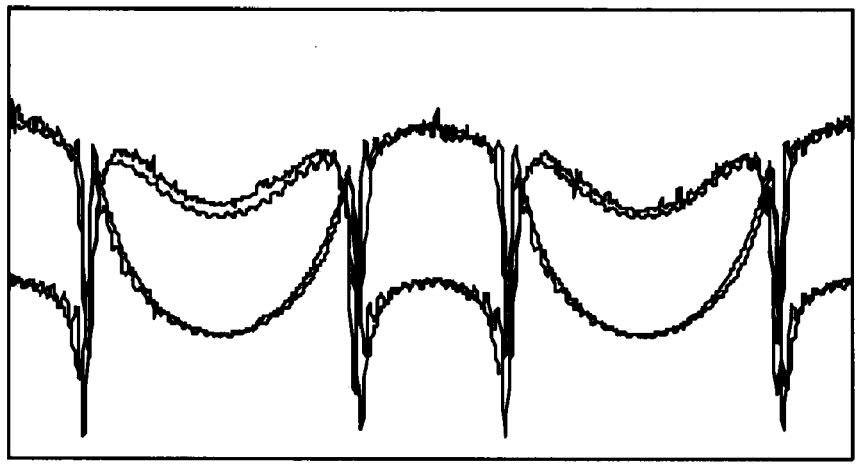
Figure 6B:
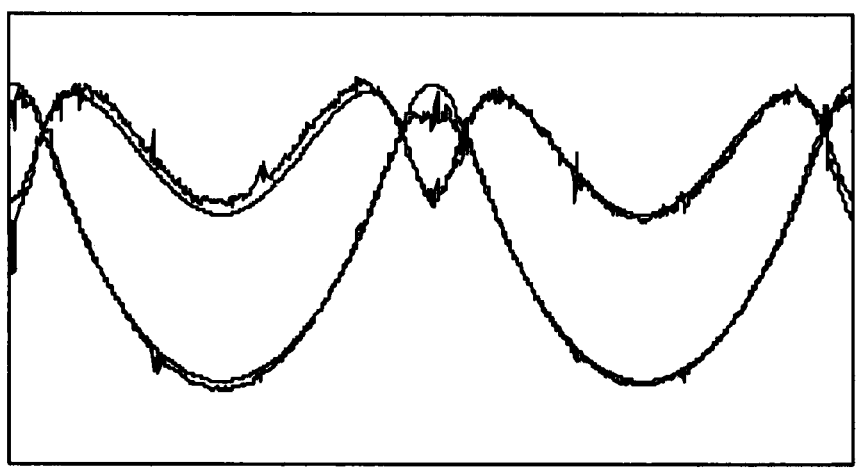
Figure 6B:
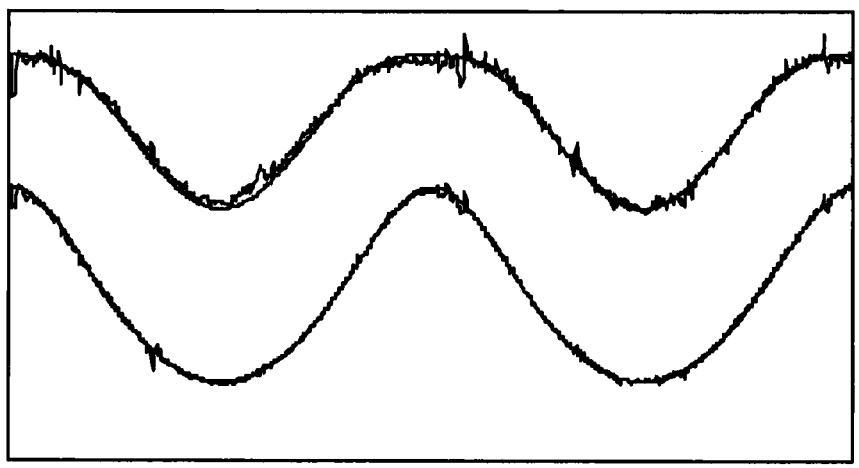

Experimental complex reflectivity data is compared to the predicted values using a library search as described above to find a best match. FIG. 6b shows a comparison of the experimental data to the best match library entry at three distinct wavelengths and angles of incidence of the illuminating light. The best match entry corresponds to a grating with a pitch of 278 nm and a depth of 45 nm in agreement with the nominal value. Thus, the diffractive properties of this structure result in clear signals leading to an accurate determination of the dimensions of the grating.

Figure 7:
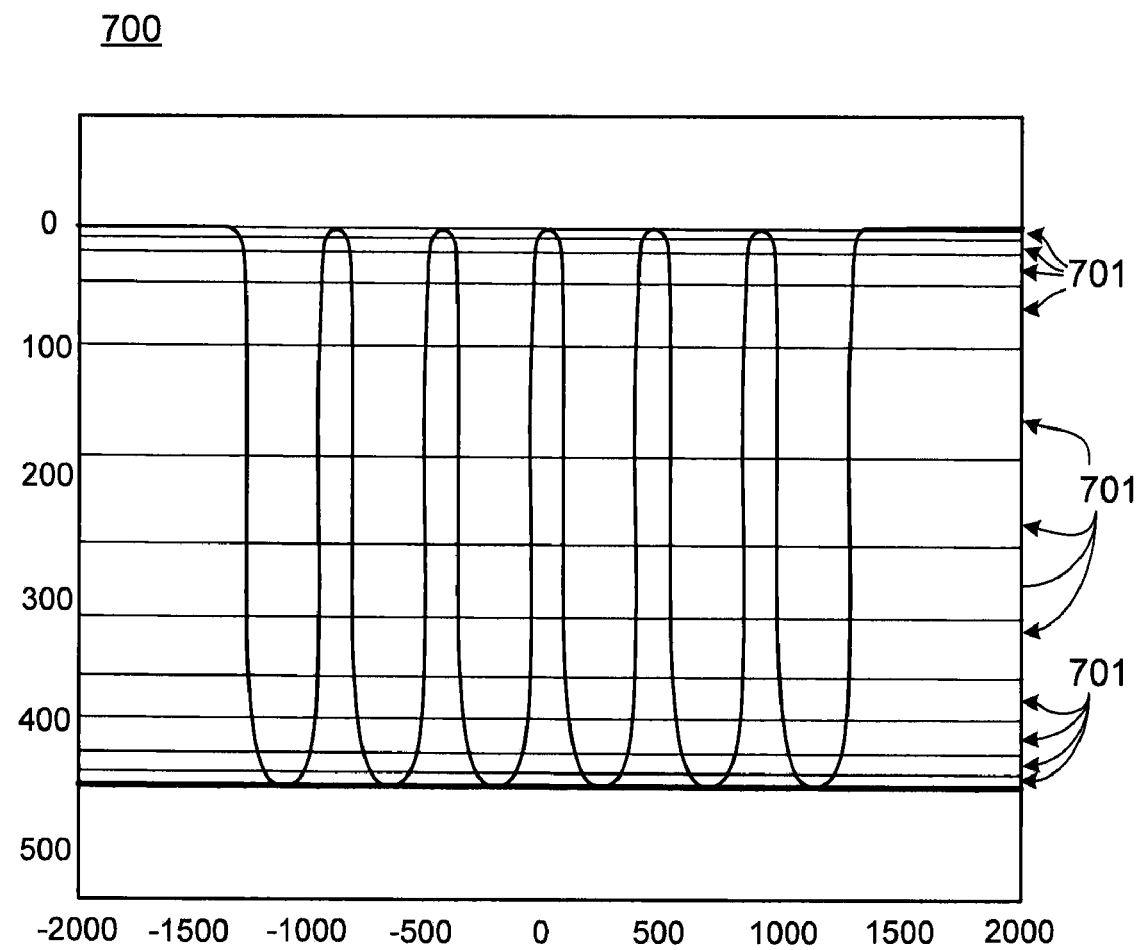
FIG. 7 shows trench structure model for RCWA analysis.

For more complex features such as semiconductor test patterns, one approach to modeling the expected signals is RCWA or related generalized solution techniques for Maxwell's equations. In some embodiments, the modeling calculations may involve "slicing" the model structure into layers as illustrated. FIG. 7 shows a model 700 for a typical surface structure formed by a shallow-trench isolation (STI) process. The structure is divided into layers 701. The shape of each layer can be characterized by one or more shape factors. Varying the shape factors for this structure to obtain the best fit of experiment to prediction leads to the desired surface structure measurement. For example, a library of predictions for a range of shape factors can be provided, and a best match can be determined using a library search as described above.

Figure 8:
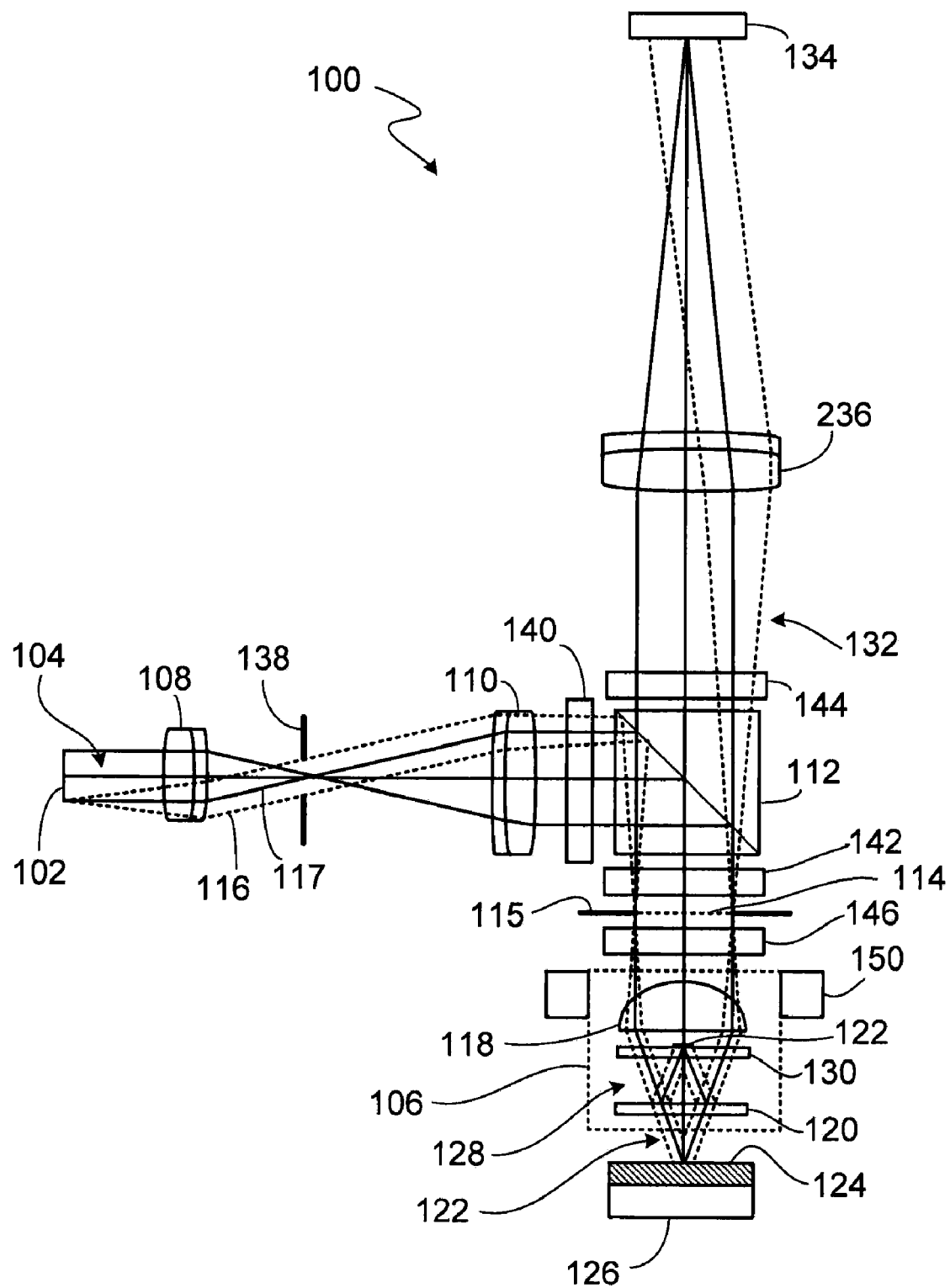
FIG. 8 is a schematic diagram of an interferometry system 100 configured to operate in a profiling mode.

Referring to FIG. 8, interferometry system 100 can switch from the above described ellipsometry (or reflectometry) mode for determining reflectivity information about the test surface, to a profiling mode for determining, for example, the topography of the test surface. This can be accomplished, for example, by replacing the relay lens 136 by another lens 236 that images test surface to the detector (rather than image the pupil plane to the detector). In this configuration, the interference signals at distinct elements of detector 134 correspond to distinct points on the test surface 124. This configuration corresponds to a conventional scanning interferometer for surface profiling.

Figure 9:
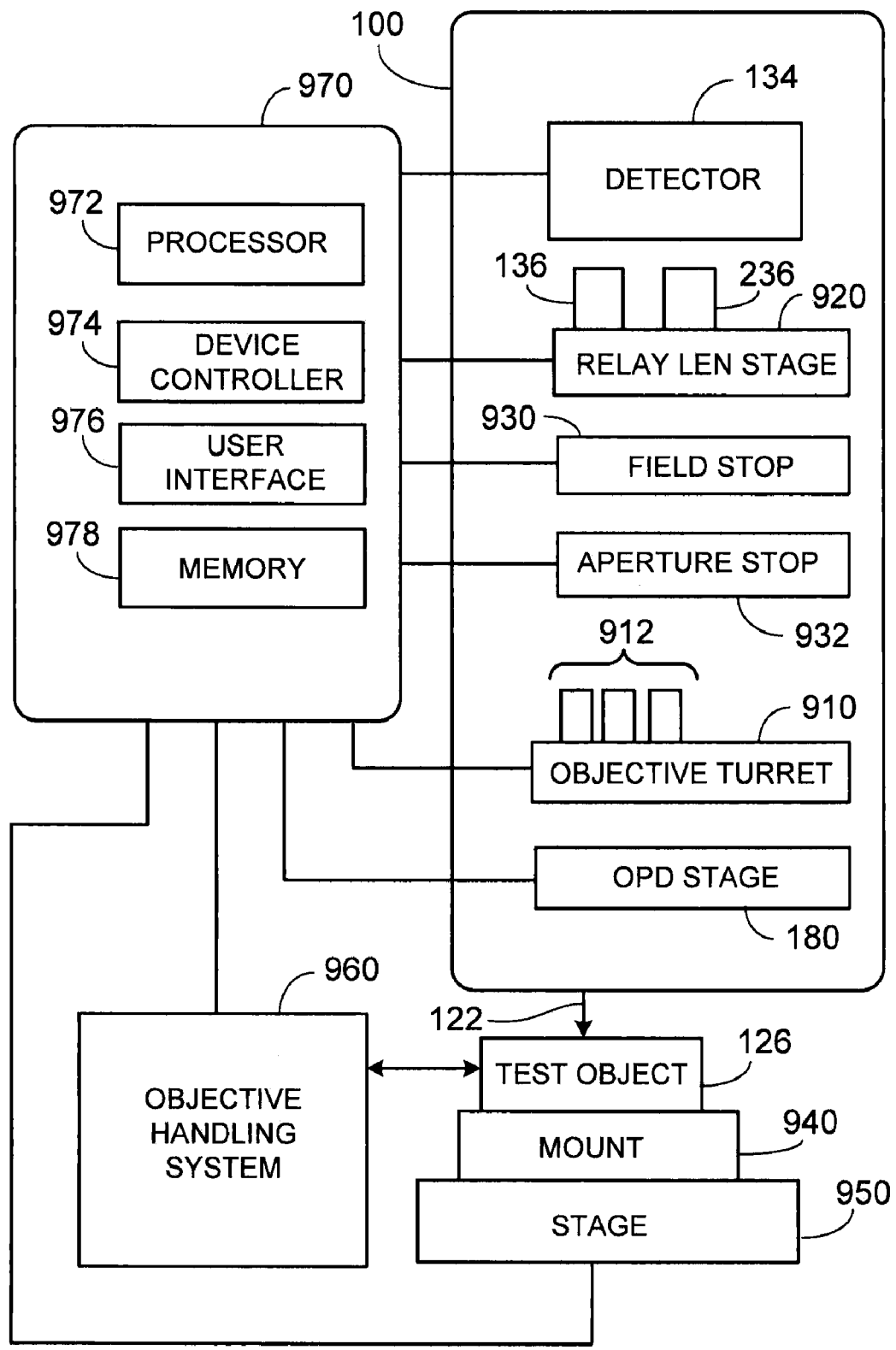
FIG. 9 is a schematic diagram of interferometry system 100 showing how various components can be adjusted in an automatic fashion.

FIG. 9 shows a schematic diagram of how various components in interferometry system 100 can be automated under the control of electronic processor 970, which, in the presently described embodiment, can include an analytical processor 972 for carrying out mathematical analyses, device controllers 974 for controlling various components in the interferometry system, a user interface 976 (e.g., a keyboard and display), and a storage medium 978 for storing calibration information, data files, a sample models, and/or automated protocols.

First, the system can include a motorized turret 910 supporting multiple objectives 912 and configured to introduce a selected objective into the path of input light 104. One or more of the objectives can be interference objectives, with the different interference objectives providing different magnifications. Furthermore, in certain embodiments, one (or more) of the interference objectives can be especially configured for the ellipsometry or reflectometry mode of operation by having polarization element 146 (e.g., a linear polarizer) attached to it. The remaining interference objectives can be used in the profiling mode and, in certain embodiments, can omit polarization element 146 so as to increase light efficiency (such as for the embodiment described above in which beam splitter 112 is a polarizing beam splitter and polarization element is 142 is a quarter wave plate). Moreover, one or more of the objectives can be a non-interferometric objective (i.e., one without a reference leg), each with a different magnification, so that system 100 can also operate in a conventional microscope mode for collecting optical images of the test surface (in which case the relay lens is set to image of test surface to the detector). Turret 910 is under the control of electronic processor 970, which selects the desired objective according to user input or some automated protocol.

Next, the system includes a motorized stage 920 (e.g., a tube lens holder) for supporting relay lenses 136 and 236 and selectively positioning one of them in the path of combined light 132 for selecting between the first mode (e.g., a reflectometry mode) in which the pupil plane 114 is imaged to the detector and the second mode (e.g., profiling or microscope mode) in which the test surface is imaged to the detector. Motorized stage 920 is under the control of electronic processor 970, which selects the desired relay lens according to user input or some automated protocol. In other embodiments, in which a translation stage is moved to adjust the position of the detector to switch between the first and second modes, the translation is under control of electronic processor. Furthermore, in those embodiments with two detection channels, each detector is coupled to the electronic processor 970 for analysis.

Furthermore, the system can include motorized apertures 930 and 932 under control of electronic processor 970 to control the dimensions of field stop 138 and aperture stop 115, respectively. Again the motorized apertures are under the control of electronic processor 970, which selects the desired settings according to user input or some automated protocol.

Also, translation stage 150, which is used to vary the relative optical path length between the test and reference legs of the interferometer, is under the control electronic processor 970. As described above, the translation stage can be coupled to adjust the position of the interference objective relative to a mount 940 for supporting test object 126. Alternatively, in further embodiments, the translation stage can adjust the position of the interferometry system as a whole relative to the mount, or the translation stage can be coupled to the mount, so it is the mount that moves to vary the optical path length difference.

Furthermore, a lateral translation stage 950, also under the control of electronic processor 970, can be coupled to the mount 940 supporting the test object to translate laterally the region of the test surface under optical inspection. In certain embodiments, translation stage 950 can also orient mount 940 (e.g., provide tip and tilt) so as to align the test surface normal to the optical axis of the interference objective.

Finally, an object handling station 960, also under control of electronic processor 970, can be coupled to mount 940 to provide automated introduction and removal of test samples into system 100 for measurement. For example, automated wafer handling systems known in the art can be used for this purpose. Furthermore, if necessary, system 100 and object handling system can be housed under vacuum or clean room conditions to minimize contamination of the test objects.

The resulting system provides great flexibility for providing various measurement modalities and procedures. For example, the system can first be configured in the microscope mode with one or more selected magnifications to obtain optical images of the test object for various lateral positions of the object. Such images can be analyzed by a user or by electronic processor 970 (using machine vision techniques) to identify certain regions (e.g., specific structures or features, landmarks, fiducial markers, defects, etc.) in the object. Based on such identification, selected regions of the sample can then be studied in the ellipsometry mode to determine sample properties (e.g., refractive index, underlying film thickness(es), under-resolved surface structures, etc.).

Accordingly, the electronic processor causes stage 920 to switch the relay lens to the one configured for the ellipsometry mode and further causes turret 910 to introduce a suitable interference objective into the path of the input light. To improve the accuracy of the ellipsometry measurement, the electronic processor can reduce the size of the field stop via motorized aperture 930 to isolate a small laterally homogenous region of the object. After the ellipsometry characterization is complete, electronic processor 970 can switch the instrument to the profiling mode, selecting an interference objective with a suitable magnification and adjusting the size of field stop accordingly. As described above, the profiling mode captures interference signals that allow reconstructing the topography of, for example, one or more interfaces that constitute the object. Notably, as described in greater detail in below, the knowledge of unresolved surface features and/or the optical characteristics of the various materials determined in the ellipsometry mode allows for correcting the calculated topography for thin film or dissimilar material effects that would otherwise distort the profile. See, for example, U.S. patent application Ser. No. 10/795,579 entitled "PROFILING COMPLEX SURFACE STRUCTURES USING SCANNING INTERFEROMETRY" and published as U.S. Patent Publication No. US-2004-0189999-A1, which was incorporated by reference above, US Patent Publication No. 20060158658A "INTERFEROMETER WITH MULTIPLE MODES OF OPERATION FOR DETERMINING CHARACTERISTICS OF AN OBJECT SURFACE", by Xavier Colonna de Lega et. al., which was incorporated by reference above, and U.S. patent application Ser. No. 11/525,355 "INTERFEROMETER AND METHOD FOR MEASURING CHARACTERISTICS OF OPTICALLY UNRESOLVED SURFACE FEATURES by Peter de Groot et. al., filed on Sep. 21, 2006, incorporated by reference herein. If desired, the electronic processor can also adjust the aperture stop diameter via motorized aperture 932 to improve the measurement in any of the various modes.

When used in conjunction with automated object handling system 960, the measurement procedure can be repeated automatically for a series of samples. This could be useful for various process control schemes, such as for monitoring, testing, and/or optimizing one or more semiconductor processing steps.

For example, the system can be used in a semiconductor process for tool specific monitoring or for controlling the process flow itself. In the process monitoring application, single/multi-layer films are grown, deposited, polished, or etched away on unpatterned Si wafers (monitor wafers) by the corresponding process tool and subsequently the thickness, under-resolved features and/or optical properties are measured using the interferometry system disclosed herein (for example, by using the ellipsometry mode, the profiling mode, or both). The average, as well as within wafer uniformity, of thickness (and/or optical properties) of these monitor wafers are used to determine whether the associated process tool is operating with targeted specification or should be retargeted, adjusted, or taken out of production use.

In the process control application, latter single/multi-layer films are grown, deposited, polished, or etched away on patterned Si, production wafers by the corresponding process tool and subsequently the thickness and/or optical properties are measured with the interferometry system disclosed herein (for example, by using the ellipsometry mode, the profiling mode, or both). Production measurements used for process control typical include a small measurement site and the ability to align the measurement tool to the sample region of interest. This site may consists of multi-layer film stack (that may itself be patterned) and thus requires complex mathematical modeling in order to extract the relevant physical parameters. Process control measurements determine the stability of the integrated process flow and determine whether the integrated processing should continue, be retargeted, redirected to other equipment, or shut down entirely.

Specifically, for example, the interferometry system disclosed herein can be used to monitor the following equipment: diffusion, rapid thermal anneal, chemical vapor deposition tools (both low pressure and high pressure), dielectric etch, chemical mechanical polishers, plasma deposition, plasma etch, lithography track, and lithography exposure tools. Additionally, the interferometry system disclosed herein can be used to control the following processes: trench and isolation, transistor formation, as well as interlayer dielectric formation (such as dual damascene).

One powerful feature of interferometry system 100 is that not only is it possible to gather rapidly and in automated fashion information about the test object for a variety of measurement modes, but also, that information determined from one mode of operation can be used to improve, for example, the speed and/or accuracy of the measurement in the mode of operation.

Figure 10:
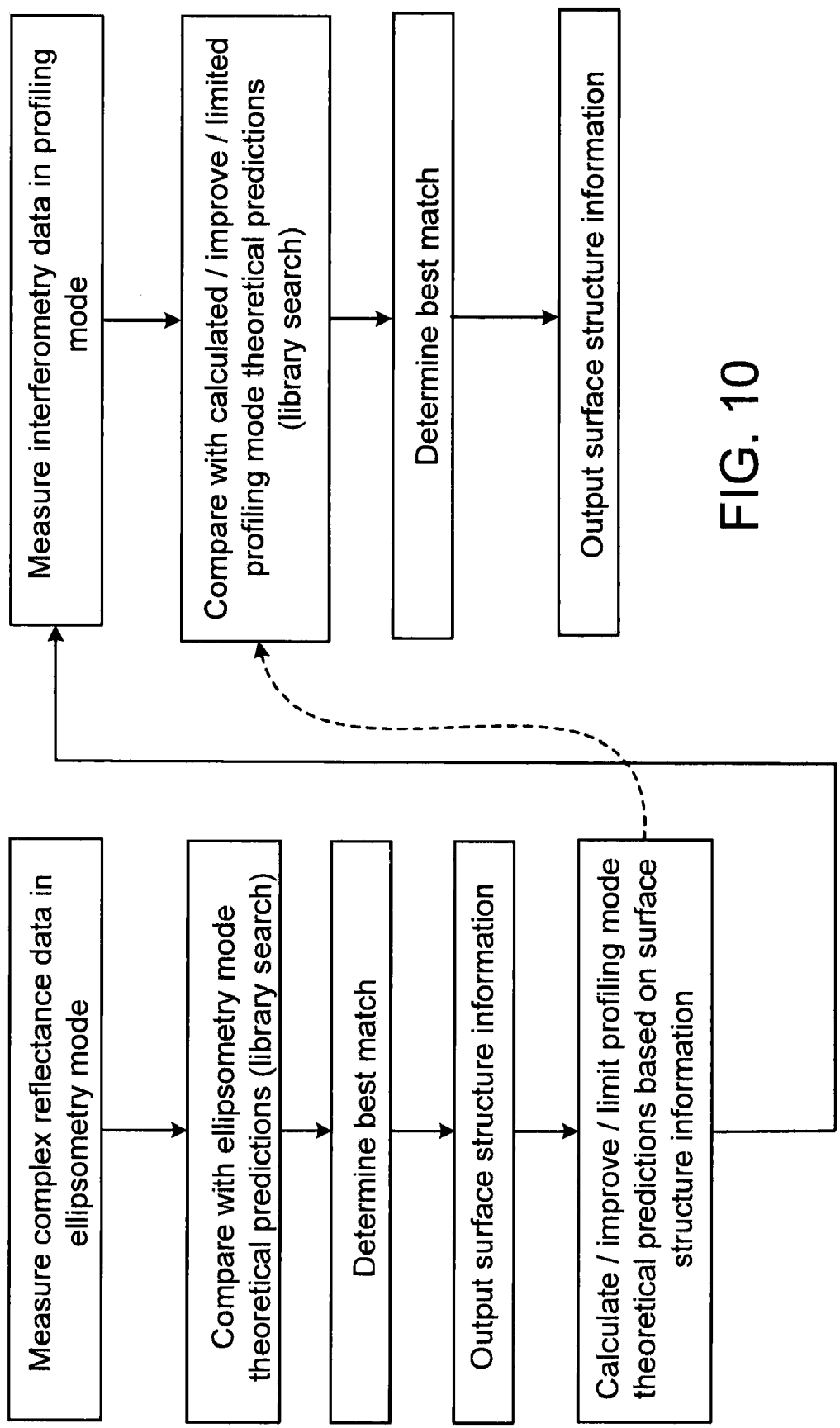
FIG. 10 is a flow diagram showing the use of an ellipsometry measurement to improve a profiling measurement.

FIG. 10 shows a flow diagram of the operation of an embodiment of an interferometer system in which information determined in the ellipsometry mode is used to improve the performance of the profiling mode. In the first step, using the above described techniques, the interferometry system operates in the ellipsometry (or reflectometry) mode to acquire complex reflectance data from a test object. Next, this data is compared with theoretical predictions based on multiple models of the test object using, for example, a library search as described above. A best match is determined, and surface structure information corresponding to the best match is output. This information may include, for example, thin film structure, surface roughness, and/or various parameters relating to under-resolved features.

The surface structure information is then used to provide theoretical predictions of interferometry data for use in the profiling mode. For example, in some embodiments, theoretical predictions are calculated based on the surface structure information to generate a library for use in the profiling mode. In some embodiments, a library of predictions has already been calculated, and the surface structure information is used to limit the scope of the library by eliminating entries based on models of the test object which are incompatible with the acquired surface structure information. In some embodiments, a library of predictions has already been calculated, and the surface structure information is used to revise or refine the theoretical predictions. Some embodiments use a combination of these approaches.

In the next step, the system is switched to the profiling mode, and interferometry data is acquired using the techniques described above. This data is compared with theoretical predictions provided using the surface structure information determined in the ellipsometry mode, using, for example, a library search. A best match is determined, and surface profile information is output.

For example, complex surface structures, such as under-resolved surface features (i.e., lateral surface features smaller than the spatial resolution of the interference microscope), may corrupt conventional surface profiling techniques based on identifying the location of the peak in the fringe contrast envelope or calculating a slope for the frequency domain phase profile. However, after the complex surface structure is characterized, surface height can be efficiently determined. For example, a comparison between the scanning interferometry signals acquired in the profiling mode and one or more model signals corresponding to the unresolved features determined in the ellipsometry mode can produce an accurate measure of the surface height. For example, as described in U.S. patent application Ser. No. 11/525,355 "INTERFEROMETER AND METHOD FOR MEASURING CHARACTERISTICS OF OPTICALLY UNRESOLVED SURFACE FEATURES by Peter de Groot et. al. filed on Sep. 21, 2006, incorporated by reference herein, a comparison between the scanning interferometry signal acquired in the profiling mode and model signals having a shape corresponding to a complex, unresolved, surface structure on the test object can produce a peak at a scan coordinate corresponding accurately to the surface height. The accuracy of model signals can be improved based on the information related to unresolved features of the surface structure determined in the ellipsometry mode. Similarly, the surface structure data can be used to improve other types of measurements performed in the profiling mode, including for example, thin film structure and/or etch depth.

As another example, in the ellipsometry mode of operation, system can determine the optical properties, including under-resolved surface features, of various materials present at different locations on an object (for example copper lines separated by dielectric regions on a semiconductor wafer). As described in detail in US Patent Publication No. 20060158658A "INTERFEROMETER WITH MULTIPLE MODES OF OPERATION FOR DETERMINING CHARACTERISTICS OF AN OBJECT SURFACE", by Xavier Colonna de Lega et. al., once these properties are known it is possible to calculate, for example, the phase change on reflection undergone by light reflecting off the object surface. In general, these phase changes are material dependent and affect the topography measurement. For example, copper regions may appear lower than they truly are with respect to the dielectric regions. However, the knowledge of the material dependent phase changes determined in the ellipsometry mode allows the electronic processor to correct the topography map to obtain the true surface topography.

Similarly, in the frequency domain, a modeled phase contribution resulting from the under-resolved features of the surface structure can be subtracted from the frequency domain phase profile and the surface height can be extracted using a conventional FDA analysis. Information related to under-resolved surface features determined in the ellipsometry mode using the above described techniques can be used to more accurately model the phase contributions.

As another example, as described in US Patent Publication No. 20060158658A "INTERFEROMETER WITH MULTIPLE MODES OF OPERATION FOR DETERMINING CHARACTERISTICS OF AN OBJECT SURFACE", by Xavier Colonna de Lega et. al., interferometry data acquired in the surface profiling mode under certain conditions (e.g. certain wavelengths or angles of incidence, exhibits a high degree of sensitivity to under-resolved surface structure features of the test object. In some embodiments, information surface structure information determined in the ellipsometry mode can be used to adjust the properties of the system in the profiling mode to ensure that the conditions for high sensitivity are met.

Figure 11:
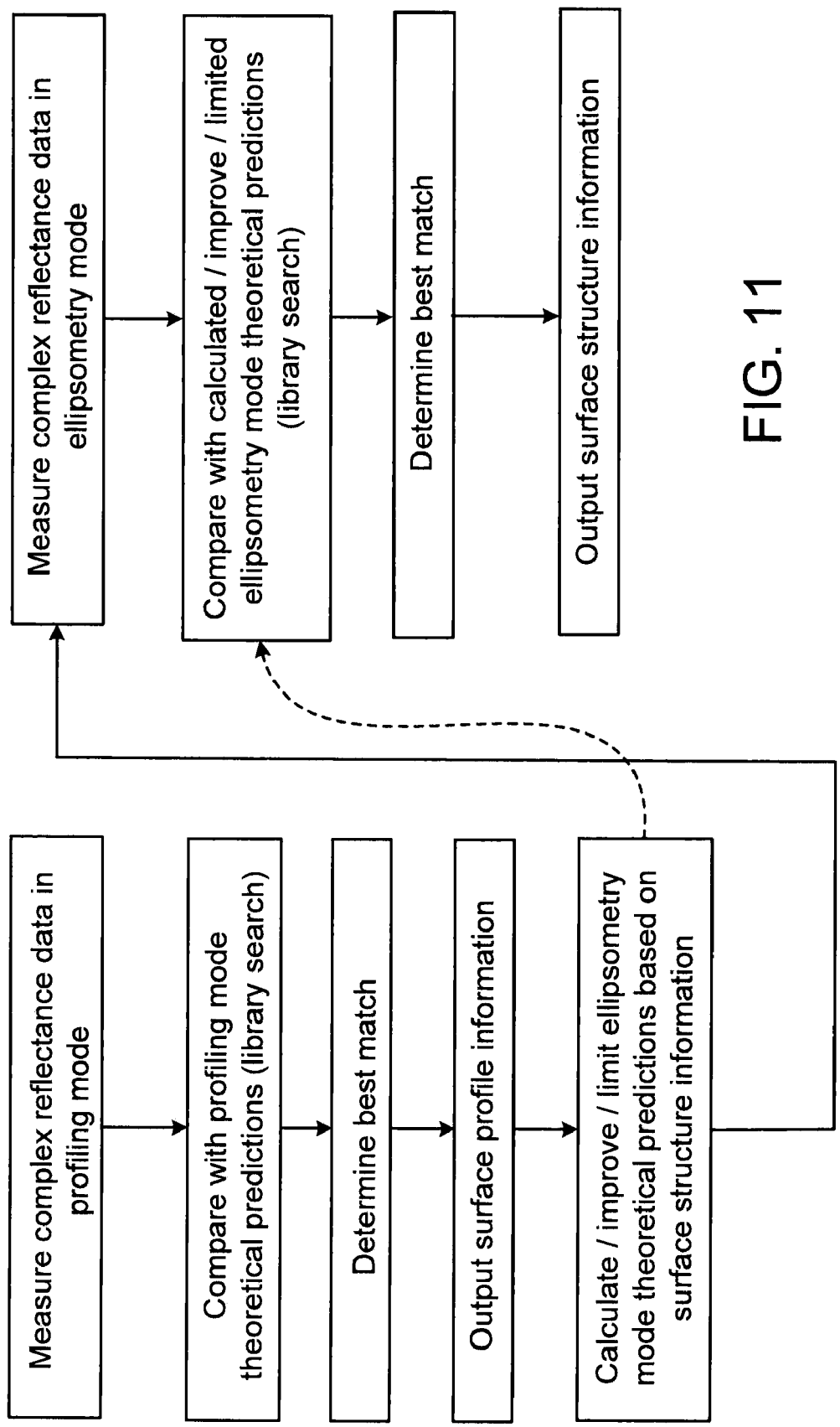
FIG. 11 is a flow diagram showing the use of a profiling measurement to improve an ellipsometry measurement.

FIG. 11 shows a flow diagram of the operation of an embodiment of an interferometer system in which information determined in the profiling mode is used to improve the performance of the ellipsometry (or reflectometry) mode. In the first step, using the above described techniques, the interferometry system operates in profiling mode to acquire interferometry data from a test object. Next, surface profile information is determined based on the interferometry data. For example, in some embodiments, the data is compared with theoretical predictions based on multiple models of the test object using, for example, a library search as described above. A best match is determined, and surface structure information corresponding to the best match is output. This information may include, for example, surface topography, thin film structure, various parameters relating to under-resolved features, etc. In some embodiments, surface profile information is determined based on the interferometry data using other methods, including, for example, those described in U.S. Pat. Publication No. US-2004-0189999-A, "PROFILING COMPLEX SURFACE STRUCTURES USING SCANNING INTERFEROMETRY", by Peter de Groot et. al., incorporated by reference herein, U.S. Pat. Application No. 60/452,465, "PROFILING COMPLEX SURFACE STRUCTURES USING SIGNALS FROM HEIGHT SCANNING INTERFEROMETRY" by Peter de Groot et. al., incorporate by reference herein, and U.S. patent application Ser. No. 11/525,355 "INTERFEROMETER AND METHOD FOR MEASURING CHARACTERISTICS OF OPTICALLY UNRESOLVED SURFACE FEATURES by Peter de Groot et. al., incorporated by reference above.

The surface structure information is then used to provide theoretical predictions of interferometry data for use in the ellipsometry mode. For example, in some embodiments, theoretical predictions are calculated based of the surface profile information to generate a library for use in the ellipsometry mode. In some embodiments, a library of predictions has already been calculated, and the surface profile information is used to limit the scope of the library by eliminating entries based on models of the test object which are incompatible with the acquired surface profile information. In some embodiments, a library of predictions has already been calculated, and the surface profile information is used to revise or refine the theoretical predictions. In some embodiments the surface profile information is used to provide corrections directly to surface structure information determined in the ellipsometry mode. Some embodiments use a combination of these approaches.

In the next step, the system is switched to the ellipsometry mode, and interferometry data is acquired using the techniques described above. This data is compared with theoretical predictions provided using the surface profile information determined in the profiling mode, using, for example, a library search. A best match is determined, and surface structure information is output.

For example, as described in US Patent Publication No. 20060158658A "INTERFEROMETER WITH MULTIPLE MODES OF OPERATION FOR DETERMINING CHARACTERISTICS OF AN OBJECT SURFACE", by Xavier Colonna de Lega et. al., interferometry data acquired in the surface profiling mode can provide information about under-resolved surface structure features of a test object. This information can be used, for example, to generate models for use in the ellipsometry mode, or to limit the range of models used in a library search.

As another example, interferometry data acquired in the surface profiling mode can provide information about, for example, thin film structure or etch depth on a test object. This information can be used, for example, to generate models for use in the ellipsometry mode, or to limit the range of models used in a library search.

The techniques described above may be applied to a variety of surface analysis problems, including: simple thin films (in which case, for example, the variable parameter of interest may be the film thickness, the refractive index of the film, the refractive index of the substrate, or some combination thereof); multilayer thin films; sharp edges and surface features that diffract or otherwise generate complex interference effects; unresolved surface roughness; unresolved surface features, for example, a sub-wavelength width groove on an otherwise smooth surface; dissimilar materials (for example, the surface may includes a combination of thin film and a solid metal, in which case the library may include both surface structure types and automatically identify the film or the solid metal by a match to the corresponding frequency-domain spectra); optical activity such as fluorescence; spectroscopic properties of the surface, such as color and wavelength-dependent reflectivity; polarization-dependent properties of the surface; deflections, vibrations or motions of the surface or deformable surface features that result in perturbations of the interference signal; and data distortions related to the data acquisition procedure, e.g. a data acquisition window that does not fully encompass the interference intensity data.

It is presently of considerable interest in the semiconductor industry to make quantitative measurements of surface structure and/or topography. Due to the small size of typical chip features, the instruments used to make these measurements typically must have high spatial resolution both parallel and perpendicular to the chip surface. Engineers and scientists use surface structure measuring systems for process control and to detect defects that occur in the course of manufacturing, especially as a result of processes such as etching, polishing, cleaning and patterning.

For process control and defect detection to be particularly useful, a surface structure and/or topography measuring system should have lateral resolution comparable to the lateral size of typical surface features, and vertical resolution comparable to the minimum allowed surface step height. Typically, this requires a lateral resolution of less than a micron, and a vertical resolution of less than 1 nanometer. It is also preferable for such a system to make its measurements without contacting the surface of the chip, or otherwise exerting a potentially damaging force upon it, so as to avoid modifying the surface or introducing defects. Further, as it is well-known that the effects of many processes used in chip making depend strongly on local factors such as pattern density and edge proximity, it is also important for a measuring system to have high measuring throughput, and the ability to sample densely over large areas in regions which may contain one or many surface features of interest.

It is becoming common among chip makers to use the so-called 'dual damascene copper' process to fabricate electrical interconnects between different parts of a chip. This is an example of a process which may be effectively characterized using a suitable surface topography system. The dual damascene process may be considered to have five parts: (1) an interlayer dielectric (ILD) deposition, in which a layer of dielectric material (such as a polymer, or glass) is deposited onto the surface of a wafer (containing a plurality of individual chips); (2) chemical mechanical polishing (CMP), in which the dielectric layer is polished so as to create a smooth surface, suitable for precision optical lithography, (3) a combination of lithographic patterning and reactive ion etching steps, in which a complex network is created includes narrow trenches running parallel to the wafer surface and small vias running from the bottom of the trenches to a lower (previously defined) electrically conducting layer, (4) a combination of metal deposition steps which result in the trenches and vias being over-filled with copper, and (5) a final chemical mechanical polishing (CMP) step in which the excess copper is removed, leaving a network of copper filled trenches (and possibly vias) surrounded by dielectric material.

Typically the thickness of the copper in the trench areas (i.e., the trench depth), and the thickness of the surrounding dielectric lie in a range of 0.2 to 0.5 microns. The width of the resulting trenches may be in a range of from 100 to 100,000 nanometers, and the copper regions within each chip may in some regions form regular patterns such as arrays of parallel lines, and in others they may have no apparent pattern. Likewise, within some regions the surface may be densely covered with copper regions, and in other regions, the copper regions may be sparse. It is important to appreciate that the polishing rate, and therefore the remaining copper (and dielectric) thickness after polishing, depends strongly and in a complex manner on the polishing conditions (such as the pad pressure and polishing slurry composition), as well as on the local detailed arrangement (i.e., orientation, proximity and shape) of copper and surrounding dielectric regions.

This 'position dependent polishing rate' is known to give rise to variable surface topography on many lateral length scales. For example, it may mean that chips located closer to the edge of a wafer on aggregate are polished more rapidly than those located close to the center, creating copper regions which are thinner than desired near the edges, and thicker than desired at the center. This is an example of a 'wafer scale' process nonuniformity—i.e., one occurring on length scale comparable to the wafer diameter. It is also known that regions which have a high density of copper trenches polish at a higher rate than nearby regions with low copper line densities. This leads to a phenomenon known as 'CMP induced erosion' in the high copper density regions. This is an example of a 'chip scale' process non-uniformity—i.e., one occurring on a length scale comparable to (and sometimes much less than) the linear dimensions of a single chip. Another type of chip scale nonuniformity, known as 'dishing', occurs within single copper filled trench regions (which tend to polish at a higher rate than the surrounding dielectric material). For trenches greater than a few microns in width dishing may become severe with the result that affected lines later exhibit excessive electrical resistance, leading to a chip failure.

CMP induced wafer and chip scale process nonuniformities are inherently difficult to predict, and they are subject to change over time as conditions within the CMP processing system evolve. To effectively monitor, and suitably adjust the process conditions for the purpose of ensuring that any non-uniformities remain within acceptable limits, it is important for process engineers to make frequent non-contact surface structure and/or topography measurements on chips at a large number and wide variety of locations. This is possible using embodiments of the interferometry techniques described above.

In the following, we describe a number of examples of types of structures that may be analyzed using the above described techniques. In general, the structures include features which can be smaller than the wavelength of light used to measure the surface structure. Although the features of the structure are not optically resolved by the measurement device, the analysis techniques described above can be used to characterize, for example, the shape of these features.

Figure 12:
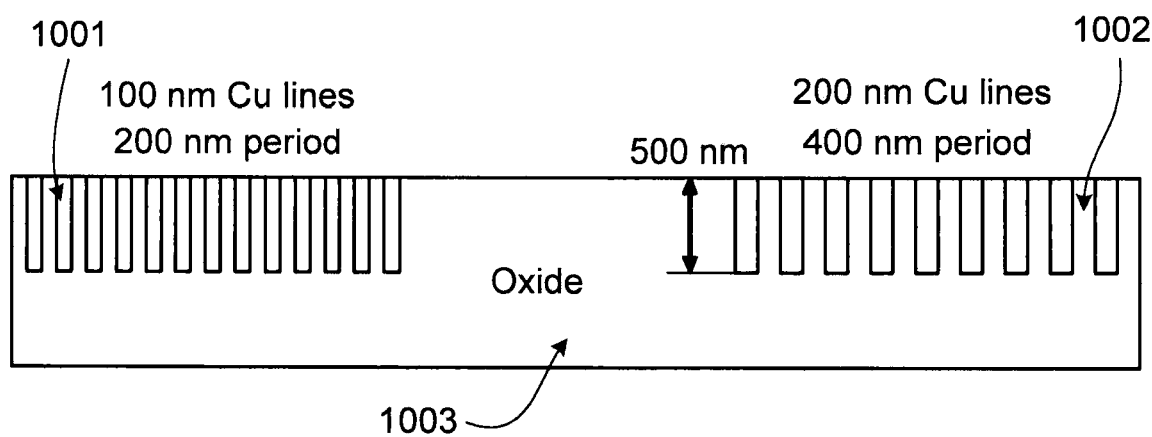
FIG. 12 is a schematic illustrating a test structures for erosion measurements for Cu damascene polishing.

FIG. 12 illustrates a test structure for erosion measurements for copper damascene polishing of, for example, the type described above. The test structure includes two groups of copper lines 1001 and 1002, in oxide layer 1003. The groups of copper lines have different line widths and line spacing (or period). The line width is smaller than the wavelength of light used to measure the surface structure. Still, the analysis techniques described above can be used to determine, for example, the different line widths and spacing and the trench depths of the lines.

Figure 13:
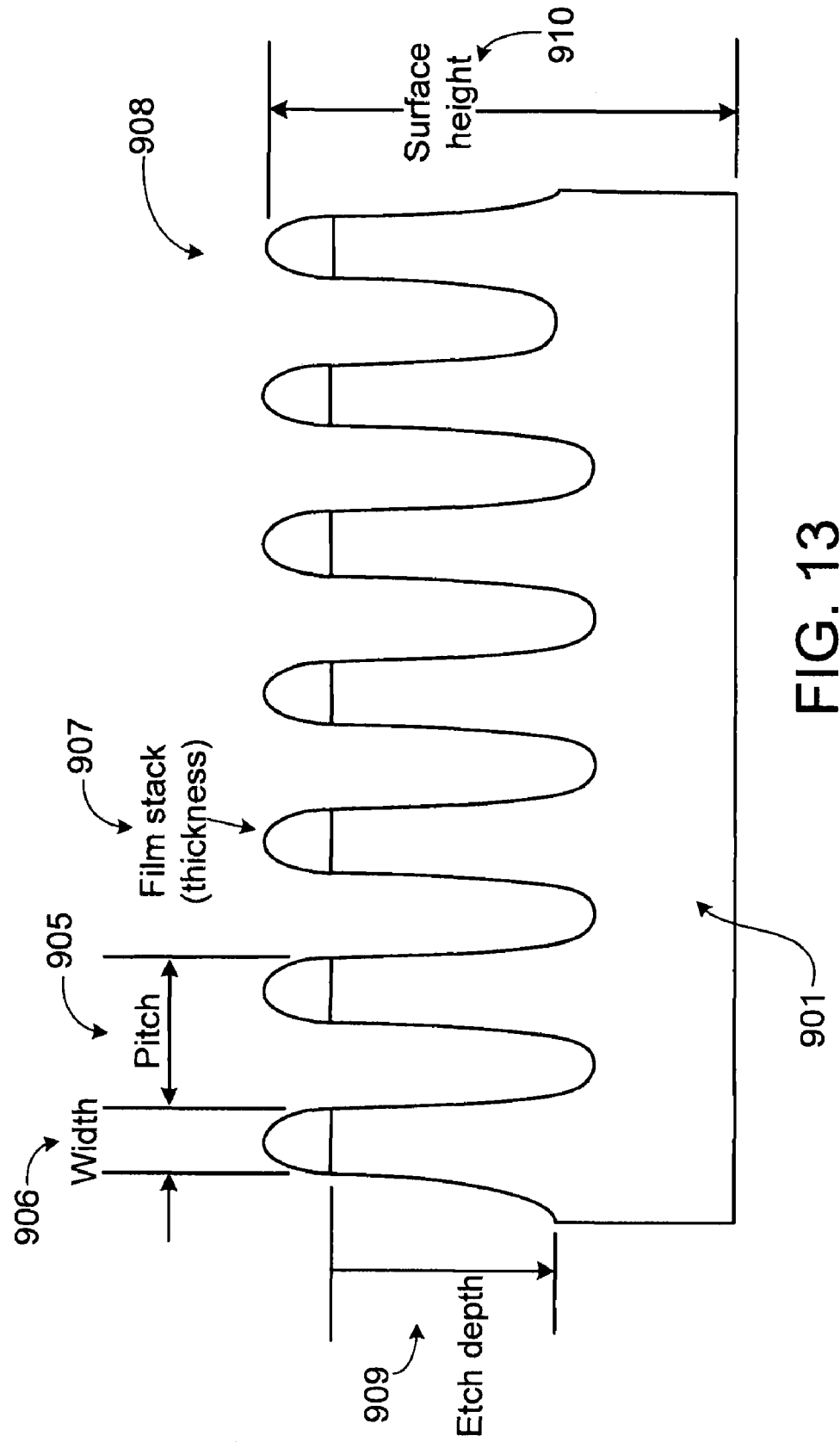
FIG. 13 is a schematic illustrating a test structure produced by a sub-wavelength etch of a film stack.

FIG. 13 illustrates a test structure produced by a sub-wavelength etch, using for example an n optical lithography tool. For example, such tools may feature the use of optical proximity corrections and/or phase shift masks to provide dimensions of patterned objects can be smaller than the wavelength used by the optical lithography tool. The structure is a film stack 1101 which has been etched with a series of lines. The line width and pitch of the etched film stack 1101 can, in general, be smaller than the wavelength of light used to measure the surface structure. The analysis techniques described above can be used to determine, for example, the line width, pitch, etch depth, and film stack thickness.

Figure 14:
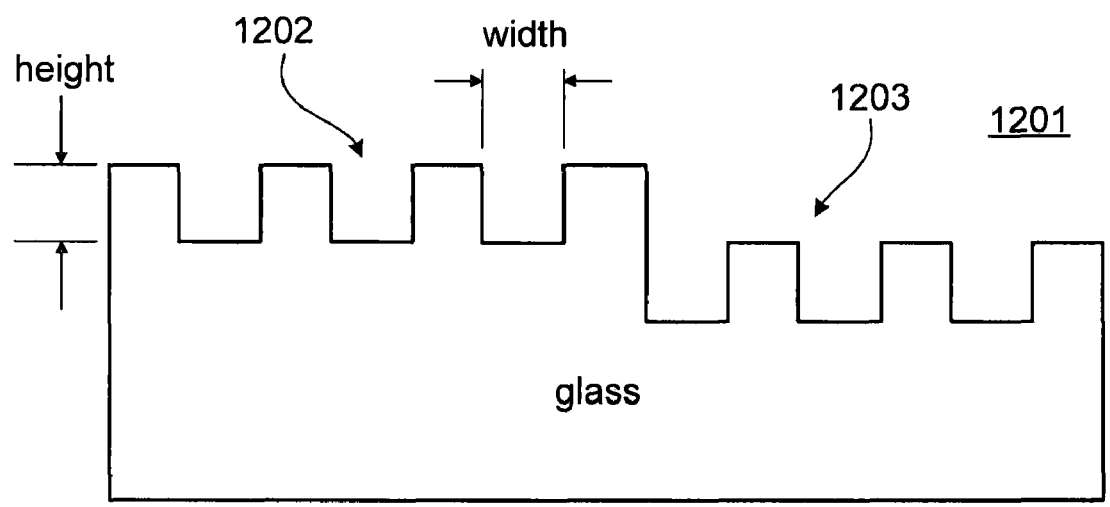
FIG. 14 is a schematic illustrating a diffractive optic.
Figure 15:
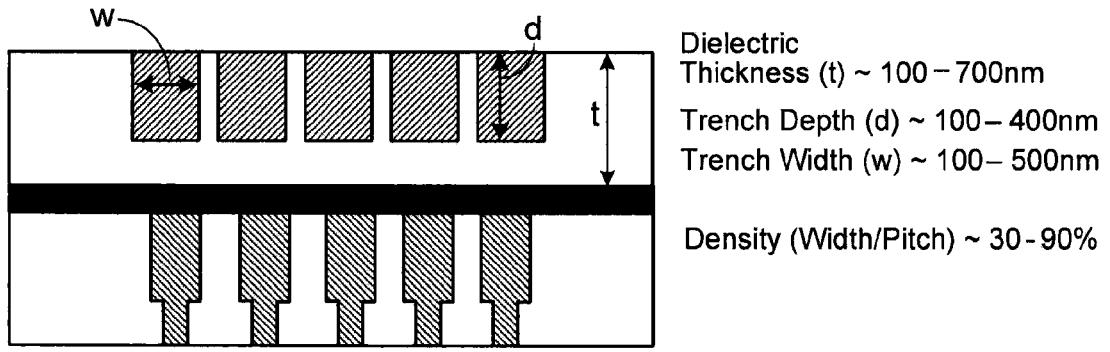
FIG. 15 is a schematic illustrating a test structure featuring complex, layered structures typical of the back end of the semiconductor processing line.
Figure 15:
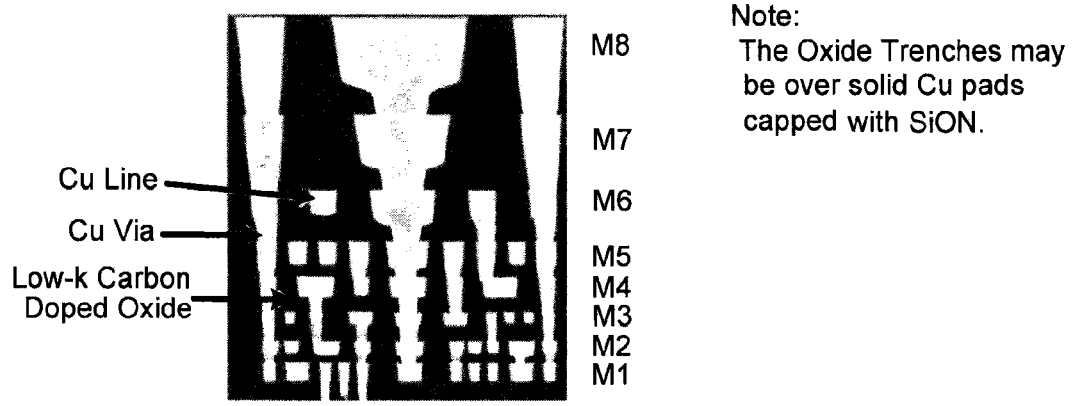

FIG. 14 illustrates diffractive optic 1201. Diffractive optic 1201 includes grating structures 1202 and 1203 characterized by a grating width and height. The analysis techniques described above can be used to determine, for example, the grating width and height FIG. 15 illustrates a complex layered test structure of the type encountered, for example, at the back end of a semiconductor processing line. The structure includes a dielectric layer with a series of trenches characterized by a trench depth, trench width, and trench density. The trenches in the oxide late are located over a group of solid copper pads capped with a layer of SiON. The analysis techniques described above can be used to determine the trench depth, trench width, and trench density.

Figure 16:
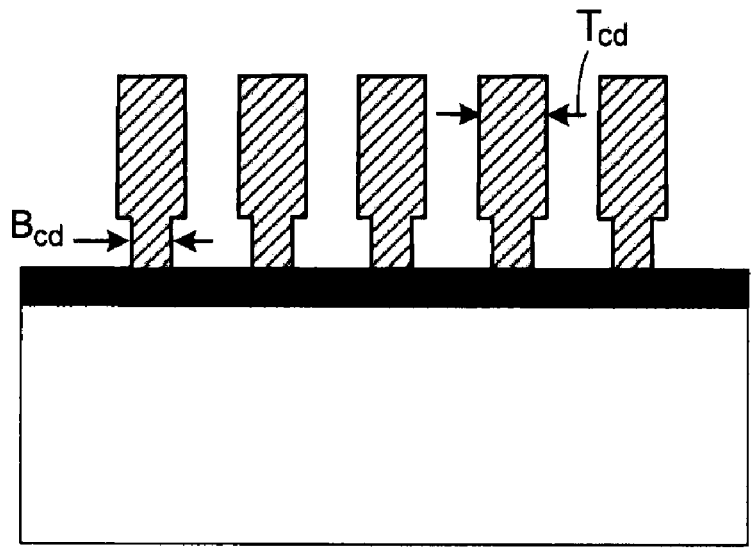
FIG. 16 is a schematic illustrating a test object with top and bottom critical dimensions.
Figure 16:
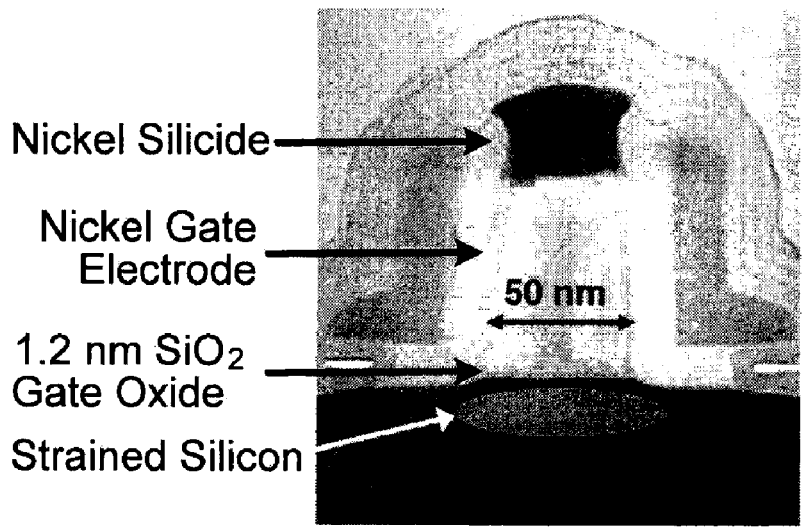

FIG. 16 illustrates a complex surface test structure 1401 of the type found in transistor fabrication. Structure 1401 includes a patterned layer of polysilicon on a substrate. The patterned layer is characterized by a top critical dimension $T_{cd}$ and a bottom critical dimension $B_{cd}$. Note that, in the illustrated example, the bottom critical dimension is less than top critical dimension, and therefore would be obscured from, for example, an optical microscope. Note also that the critical dimensions are on the scale of a few tens of nanometers, and thus would generally be optically unresolved by the measurement device. Still, the analysis techniques described above can be used to determine the top and bottom critical dimensions.

The interferometer embodiments described above include an interference objective of the Mirau-type and of the Linnik-type. In the Mirau, the beam splitter in the interference objective directs the reference light back along the optical axis for the test light. In the Linnik-type, the beam splitter is positioned prior to the objective lens for the test surface (with respect to the input light) and directs the test and reference light along different paths. A separate objective lens is used to focus the reference light to the reference lens. In other words, the beam splitter separates the input light into the test and reference light, and separate objective lenses then focus the test and reference light to respective test and reference surfaces. Ideally the two objective lenses are matched to one another so that the test and reference light have similar aberrations and optical paths.

In other embodiments, the interferometry system can instead use a different type of interference objective, such as a Michelson objective, in which the beam splitter directs the reference light away from the optical axis of the test light (e.g., the beam splitter can be oriented at 45 degrees to the input light so the test light and reference travel at right angles to one another). In such cases, the reference surface can be positioned outside of the path of the test light.

In some embodiments, the interferometry system may include any of the following features: a spectrally narrow-band light source with a high numerical aperture (NA) objective; a spectrally broad band light source; a combination of a high NA objective and a spectrally broadband source; an interferometric microscope objectives, including oil/water immersion and solid immersion types, in e.g. Michelson, Mirau or Linnik geometries; a sequence of measurements at multiple wavelengths; unpolarized light; and polarized light, including linear, circular, or structured. For example, structured polarized light may involve, for example, a polarization mask, generating different polarizations for different segments of the illumination or imaging pupils, so as to reveal polarization-dependent optical effects attributable to surface characteristics. The interferometer may also include the overall system calibration, described above.

Additional interferometer configurations are also possible. For example, the system can be configured to collect test light that is transmitted through the test sample and then subsequently combined with reference light. For such embodiments, for example, the system can implement a Mach-Zehnder interferometer with dual microscope objectives on each leg.

The light source in the interferometer may be any of: an incandescent source, such as a halogen bulb or metal halide lamp, with or without spectral bandpass filters; a broadband laser diode; a light-emitting diode; a combination of several light sources of the same or different types; an arc lamp; any source in the visible spectral region; any source in the IR spectral region, particularly for viewing rough surfaces & applying phase profiling; and any source in the UV spectral region, particularly for enhanced lateral resolution. For broadband applications, the source preferably has a net spectral bandwidth broader than 5% of the mean wavelength, or more preferably greater than 10%, 20%, 30%, or even 50% of the mean wavelength. For tunable, narrow-band applications, the tuning range is preferably broad (e.g., greater than 50 nm, greater than 100 nm, or greater than even 200 nm, for visible light) to provide information over a wide range of wavelengths, whereas the spectral width at any particular setting is preferable narrow, to optimize resolution, for example, as small as 10 nm, 2 nm, or 1 nm. The source may also include one or more diffuser elements to increase the spatial extent of the input light being emitted from the source.

In some embodiments, the light source and the interferometer may be configured to provide Koehler illumination of the pupil plane of the interference objective. In other embodiments, the illumination of the pupil plane is of a type other than Koehler illumination, for example critical or Nelsonian illumination.

Furthermore, the various translations stages in the system, such as translation stage 150, may be: driven by any of a piezo-electric device, a stepper motor, and a voice coil; implemented opto-mechanically or opto-electronically rather than by pure translation (e.g., by using any of liquid crystals, electro-optic effects, strained fibers, and rotating waveplates) to introduce an optical path length variation; any of a driver with a flexure mount and any driver with a mechanical stage, e.g. roller bearings or air bearings. As noted above, while the phase-shifting for the scanning interferometry signal is often done by using a mechanical translation stage, it is also possible to vary the phase between the test and reference legs of the interferometer by varying the wavelength of the source when there is a non-zero optical path length difference between the test and reference legs.

The electronic detector can be any type of detector for measuring an optical interference pattern with spatial resolution, such as a multi-element CCD or CMOS detector.

In certain embodiments, system calibration is performed that includes calculating the angle of incidence of a beam bundle at the test surface based on the location of the source point in the pupil plane. In other words, we want to assign an angle of incidence to each pixel in the detector corresponding to the image of the pupil plane. This can be accomplished, for example, by performing a measurement with a narrowband filter so that the light detected by the detector is essentially monochromatic and has a known wavelength. In this case, the frequency of the interference signal is proportional to the source wavelength time the cosine of the angle of incidence. The signal frequency can be calculated by a Fourier transform of the signal and the angle of incidence can be derived from the knowledge of the scan rate of the translation stage and the source wavelength.

Furthermore, to the extent the scan rate of the translation stage is initially unknown, it can be determined by locating the pixel on the detector whose interference signal has the largest frequency. According to the frequency's cosine dependence on the angle of incidence, this pixel corresponds to normal incidence and so the stage speed can be extracted directly from the measured frequency and knowledge of the source wavelength.

Note that a priori information on the way the microscope objective maps angles in object space onto pupil positions can also be used to improve the quality of this calibration. For example, a typical objective is corrected for coma (a geometric aberration), which implies that the ray mapping at the pupil should nominally obey the so-called "Abbe sine condition." This condition means that the radial distance of a source point from the optical axis at the pupil is directly proportional to the sine of the angle of incidence in object space. One can thus calculate the angle of incidence for each pixel and then fit a global function derived from the sine condition to provide an analytical function mapping pupil position to angle of incidence.

In certain embodiments, the procedure outlined above can be repeated for different nominal source wavelengths so that chromatic variations of the angular mapping are taken into account. A by-product of the fitting procedure is the pixel position of the optical axis at the pupil. That information is also recorded as a function of wavelength and can be used later on to apply corrections to angle of incidence calculations.

For certain embodiments, the calibration also involves calculating the value of the various system parameters as described in US Patent Publication No. 20060158657"A INTERFEROMETER FOR DETERMINING CHARACTERISTICS OF AN OBJECT SURFACE, INCLUDING PROCESSING AND CALIBRATION" by Xavier Colonna de Lega et. al., incorporated by reference above.

Any of the computer analysis methods described above can be implemented in hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis method can also be implemented as a computer-readable storage medium, configured with a computer program, where the storage medium so configured causes a computer to operate in a specific and predefined manner to perform the functions described herein.

While the specific descriptions above often refer to a scanning interferometry signal for which limited coherence in the interferometry system causes localization of the interference fringes; for many embodiments, it is also possible to extract information about complex surface features from interferometry signal(s) not having such fringe localization.

For example, interferometry signals from different locations of the test object that do not have fringe localization can still be used to generate an apparent surface profile for the test object, and that apparent surface profile, or information derived there from, can be compared to models of the expected response for different values of lateral surface features of the test object that are not-resolved or obscured in the apparent surface profile to determine information about such under-resolved features in much the same way as that described above for low coherence scanning interferometry signals. Techniques for extracting surface profile information from such "high" coherence interferometry signals are generally referred to as phase shifting interferometry (PSI) algorithms, and are well-known in the art. See, for example, the background and contents of U.S. Pat. No. 6,359,692, entitled "METHOD AND SYSTEM FOR PROFILING OBJECTS HAVING MULTIPLE REFLECTIVE SURFACES USING WAVELENGTH-TUNING PHASE-SHIFTING INTERFEROMETRY," the contents of which are incorporated herein by reference. To generate the interferometry data for such PSI analysis, the interferometry signal for a given pixel can be generating by mechanically varying the optical path length difference between the reference and measurement legs, or by varying the wavelength of the light for a fixed, non-zero optical path length difference between the reference and measurement legs.

A number of embodiments have been described. Other embodiments are in the claims.

What is claimed is:

1. An apparatus comprising:
    an interferometry system comprising an objective, the interferometry system being configured to operate in a first mode to produce a first set of multiple interferometry signals corresponding to different illumination angles of a test object by test light and in a second mode to produce a second set of multiple interferometry signals corresponding to different surface locations of a test object, wherein both the first and second modes use the objective to direct light to and collect light from the test object; and
    an electronic processor coupled to the interferometry system configured to receive the first set of interferometry signals and programmed to compare information derivable from the first set of multiple interferometry signals to information corresponding to multiple models of the test object to determine information related to one or more under-resolved features of the test object, and output the information.

2. The apparatus of claim 1, wherein the apparatus is configured to selectively switch between the first and second modes.

3. The apparatus of claim 1, wherein the apparatus is configured to simultaneously provide measurements in both modes.

4. The apparatus of claim 1, wherein the interferometry system comprises at least one electronic detector, and in the first mode different elements of the detector correspond to different illumination angles of the test surface by test light in the interferometry system.

5. The apparatus of claim 4, wherein the first mode corresponds to an ellipsometry mode that measures the reflectivity of the test surface over the range of angles and wavelengths for one or more selected polarizations.

6. The apparatus of claim 5, wherein the reflectivity is a complex reflectivity.

7. The apparatus of claim 4, wherein the first mode corresponds to a reflectometry mode that measures the reflectivity of the test surface over the range of angles and wavelengths for unpolarized light.

8. The apparatus of claim 7, wherein the reflectivity is a complex reflectivity.

9. The apparatus of claim 4, wherein interferometry system images a pupil plane for test light directed to the test surface to the detector.

10. The apparatus of claim 1, wherein the interferometry system comprises at least one electronic detector, and in the second mode different elements of the detector correspond to different locations of the test surface illuminated by test light in the interferometry system.

11. The apparatus of claim 10, wherein the interferometry system is configured to image the test surface to the detector.

12. The apparatus of claim 11, wherein the second mode is a profiling mode.

13. The apparatus of claim 1, wherein the electronic processor is further configured to receive the first and second sets of interferometry signals and programmed to determine information about the test object, and output the information about the test object.

14. The apparatus of claim 13, wherein the electronic processor is further configured to use the information derived in one mode of operation to assist in determining further information about the test object when using the other mode of operation.

15. The apparatus of claim 14, wherein the electronic processor is configured to use the information related to under-resolved features of the test object determined in the first mode of operation to assist in determining further information about the test object when using the other mode of operation.

16. The apparatus of claim 14, wherein the electronic processor is configured to:
    i) derive multiple models of the test object based on the information related to under-resolved features of the test object determined in the first mode of operation and
    ii) compare information derivable from the second set of multiple interferometry signals to information corresponding to the multiple models of the test object based on the information related to under-resolved features to determine further information related to the test object, and output the information.

17. The apparatus of claim 16 wherein the further information is a surface profile.

18. The apparatus of claim 1, wherein the interferometry system is further configured to selectively operate in a non-interferometric microscopy mode to measure non-interferometric optical images of the test surface.

19. The apparatus of claim 1, wherein the test object comprises a grating structure and the information related to one or more under-resolved features of the test object comprises one of: a grating pitch, a grating depth.

20. The apparatus of claim 1, wherein the test object comprises one or more thin films, and the information related to one or more under-resolved features of the test object comprises a thin film thickness.

21. The apparatus of claim 1, wherein the test object comprises a structure characterized by a critical dimension, and the information related to one or more under-resolved features of the test object comprises the critical dimension.

22. The apparatus of claim 1, wherein the interferometry system comprises an interferometer that includes the objective, the interferometer being configured to direct test light to a test surface and subsequently combine it with reference light to form an interference pattern, the test and reference light being derived from a common source;
    an electronic detector;
    and one or more optics configured to direct at least a portion of the combined light to the detector so that different regions of the detector correspond to different illumination angles of the test surface by the test light, wherein the interferometer system is configured to operate in the first mode to direct the combined light to the detector so that the different regions of the detector correspond to the different illumination angles of the test surface by the test light and a second mode in which the different regions of the detector correspond to the different regions of the test surface illuminated by the test light to enable a profiling mode of operation.

23. The apparatus of claim 22, further comprising a stage configured to adjust the position of the detector relative to the one or more optics to switch between the first and second modes of operation.

24. The apparatus of claim 23, further comprising an electronic controller coupled to the detector stage and configured to adjustably cause the stage to switch between the first and second modes of operation.

25. The apparatus of claim 22, wherein the one or more optics comprise a first set of one or more optics for operating in the first mode of operation and a second set of one or more optics for operating in the second mode of operation.

26. The apparatus of claim 25, further comprising a multi-position optics holder supporting the first and second set of optics and configured to adjustably position one of the first and second sets and not the other of the first and second sets in the path of the combined light being directed to the detector to switch between the first and second modes.

27. The apparatus of claim 26, wherein the multi-position optics holder is motorized, and the apparatus further comprises an electronic controller coupled to the motorized multi-position optics holder to selectively cause the multi-position optics holder to switch between the first and second modes of operation.

28. The apparatus of claim 22, further comprising a second set of one or more optics, a beam splitter positioned to direct a first portion of the combined to light to the first of optics and direct a second portion of the combined light to the second set of optics, and a second electronic detector, wherein the second set of optics is configured to direct the second portion of the combined light to the second electronic detector so that different regions of the second detector correspond to the different regions of the test surface illuminated by the test light.

29. The apparatus of claim 22, wherein the interferometer comprises a multi-position mount configured to support multiple objectives including the objective and position a selected objective in the path of input light from the common source, wherein at least one of the multiple objectives is an interference objective.

30. The apparatus of claim 29, wherein the multi-position mount is motorized, and the apparatus further comprises an electronic controller coupled to the multi-position mount to selectively cause the mount to switch between objectives.

31. The apparatus of claim 29, wherein the multiple objectives comprise two different interference objectives, only one of which includes a polarization optic.

32. The apparatus of claim 29, wherein the multiple objectives comprise a non-interferometric objective, which when positioned in the path of the input light enables the apparatus to operate in a non-interferometric, microscope mode.

33. The apparatus of claim 4, wherein the interferometer system comprises a scanning interferometer.

34. The apparatus of claim 33, wherein the processor is configured to transform one or more of the interference signals from the first set of interferometry signals into a frequency domain to extract angularly resolved and wavelength-resolved information about the test surface based on the transformed signals.

35. The apparatus of claim 33, wherein the information comprises reflectivity.

36. A method comprising:
using an interferometry system comprising an objective in a first mode of operation to produce a first set of multiple interferometry signals corresponding to different illumination angles of a test object by test light;
using the same interferometry system in a second mode to produce a second set of multiple interferometry signals corresponding to different surface locations of a test object, wherein using the interferometry system in the first and second modes both comprise using the objective to direct light to and collect light from the test object;
comparing information derivable from the first set of multiple interferometry signals to information corresponding to multiple models of the test object to determine information related to one or more under-resolved features of the test object; and outputting the information.

37. The method of claim 36, wherein the one or more under-resolved features of the test object correspond to one or more of a pitch, a modulation depth, and an element width for an under-resolved patterned structure on the test object.

38. The method of claim 36, wherein the one or more under-resolved features of the test object correspond to at least a modulation depth for an under-resolved patterned structure on the test object.

39. The method of claim 37, wherein at least some of the interferometry signals are derived from an illumination of the test object whose polarization is oriented with respect to elements of the under-resolved patterned structure.

40. The method of claim 39, wherein the polarization is a linear polarization aligned orthogonal to the length of the individual elements that define the under-resolved patterned structure.

41. The method of claim 36, wherein the one or more under-resolved features of the test object correspond to one or more of a height and a position of a step on the test object.

42. The method of claim 36, wherein the test object comprises a patterned structure whose individual elements are obscured.

43. The method of claim 42, wherein the information related to the under-resolved feature corresponds to one or more of a modulation depth and an element width for the patterned structure.

44. The method of claim 36 wherein the models are generated computationally using rigorous coupled wave analysis.

45. The method of claim 36, wherein the models are generated empirically from test objects having known properties.

46. The method of claim 36, wherein the information about the under-resolved surface feature is outputted to a user.

47. The method of claim 36, wherein the information about the under-resolved surface feature is outputted to an automated process control system for semiconductor manufacturing.

48. The method of claim 36, wherein the interferometry signals are scanning interferometry signals.

49. The method of claim 48, wherein the scanning interferometry signal is produced by directing test light to interfere with reference light on a detector, and varying an optical path length difference from a common source to the detector between interfering portions of the test and reference light, wherein the test and reference light are derived from the common source, and wherein the scanning interferometry signal corresponds to an interference intensity measured by the detector as the optical path length difference is varied.

50. The method of claim 49, further comprising producing the scanning interferometry signal.

51. The method of claim 50, the further comprising transforming one or more of the interferometry signals from the first set of interferometry signals into a frequency domain to a frequency domain to extract angularly resolved and wavelength-resolved information about the test surface based on the transformed signals.

52. The method of 36, wherein the interferometry system comprises at least one electronic detector, and in the first mode different elements of the detector correspond to different illumination angles of the test surface by test light in the interferometry system.

53. The method 52, wherein the information derivable from the first set of multiple interferometry signals comprises the reflectivity of the test surface over the range of angles and wavelengths for one or more selected polarizations.

54. The method of claim 53, wherein the reflectivity is a complex reflectivity.

55. The method of claim 51, wherein the information derivable from the first set of multiple interferometry signals comprises the reflectivity of the test surface over the range of angles and wavelengths for unpolarized light.

56. The method of claim 55, wherein the reflectivity is a complex reflectivity.

57. The method of claim 52, further comprising imaging a pupil plane for test light directed to the test surface to the detector.

58. The method of claim 36, further comprising:
determining information about the test object based on information derivable from the first and second sets of interferometry signals; and outputting the information about the test object.

59. The method of claim 58, wherein the determining information about the test object comprises using information derived in one mode of operation to assist in determining further information about the test object when using the other mode of operation.

60. The method of claim 58, wherein the determining information about the test object comprises using the information related to the one or more under-resolved features of the test object determined in the first mode of operation to assist in determining further information about the test object when using the other mode of operation.

61. The method of claim 60 wherein the determining information about the test object comprises:
deriving multiple models of the test object based on the information related to under-resolved features of the test object determined in the first mode of operation;
comparing information derivable from the second set of multiple interferometry signals to information corresponding to the multiple models of the test object based on the information related to under-resolved features to determine further information related to the test object; and outputting the further information related to the test object.

62. The apparatus of claim 58 wherein the further information about the test object comprises a surface profile.

63. The method of claim 36, wherein using the interferometer in the first mode of operation comprises producing a first set of multiple interference signals illuminating the test object with light having a first polarization state, and producing another first set of interference signals illuminating the test object with light having a second polarization state, wherein the first and second polarization states are different.

64. The method of claim 63, wherein the first and second polarization states are orthogonal.

65. The method of claim 64, wherein the under-resolved features comprises a grating and the first polarization state is a linear polarization state aligned orthogonal to a plurality of the grating's lines.

* * * * *

UNITED STATES PATENT AND TRADEMARK OFFICE
CERTIFICATE OF CORRECTION

| | | |
|---|---|---|
| PATENT NO. | : 7,924,435 B2 | Page 1 of 1 |
| APPLICATION NO. | : 11/963693 | |
| DATED | : April 12, 2011 | |
| INVENTOR(S) | : Xavier Colonna De Lega et al. | |

It is certified that error appears in the above-identified patent and that said Letters Patent is hereby corrected as shown below:

Cover page, column 2 (Abstract), line 12, after "or" insert --more--.

Column 33, line 28, after "combined" delete "to".

Column 33, line 28, after "first" insert --set--.

Column 34, claim 40, line 25, after "orthogonal" insert --, parallel, or at 45°--.

Column 34, claim 51, line 62, after "50," delete "the".

Column 34, claim 51, lines 64 and 65, after "domain to" delete "a frequency domain to".

Column 35, claim 52, line 1 after "method of" insert --claim--.

Column 35, claim 53, line 6 after "method" insert --of claim--.

Signed and Sealed this
Fifth Day of July, 2011

David J. Kappos
*Director of the United States Patent and Trademark Office*